United States Patent [19]
Johnson et al.

[11] Patent Number: 6,066,101
[45] Date of Patent: May 23, 2000

[54] AIRFLOW PERTURBATION DEVICE AND METHOD FOR MEASURING RESPIRATORY RESISTANCE

[75] Inventors: Arthur T. Johnson, Darlington; Christopher G. Lausted, Adelphi, both of Md.

[73] Assignee: University of Maryland, College Park, Md.

[21] Appl. No.: 09/062,587

[22] Filed: Apr. 20, 1998

[51] Int. Cl.[7] .................................................. A61B 5/08
[52] U.S. Cl. ............................................ 600/533; 600/529
[58] Field of Search .................................. 600/532, 533, 600/529, 534, 538

[56] References Cited

U.S. PATENT DOCUMENTS

| | | | |
|---|---|---|---|
| 3,621,833 | 11/1971 | Crane ........................................ | 600/533 |
| 4,220,161 | 9/1980 | Berlin et al. . | |
| 4,856,532 | 8/1989 | Johnson .................................. | 600/533 |
| 5,233,998 | 8/1993 | Chowienczyk et al. ................. | 128/720 |
| 5,462,061 | 10/1995 | Malouvier et al. ...................... | 600/533 |
| 5,522,397 | 6/1996 | Vermaak .................................. | 600/533 |
| 5,582,182 | 12/1996 | Hillsman ................................. | 600/533 |
| 5,743,270 | 4/1998 | Gazzara et al. .......................... | 128/724 |

OTHER PUBLICATIONS

Innov. Tech. Biol. Med.; vol. 6, No. 4, 1985, "Model Analysis of the Airflow Perturbation Device", Lin et al. pp. 461–472.

"Airflow Resistance of Conscious Boars", Johnson et al, *Transactions of the ASAE* 1983, pp. 1150–1152.

"Airflow Perturbation Device for Respirator Research and Medical Screening", Johnson et al, *Journal of the ISRP*, vol. 2, Issue 4, Oct.–Dec. 1984, pp. 338–346.

"Airflow Perturbation Device for Measuring Airways Resistance of Animals", Johnson et al, *Transactions of the ASAE*, vol. 26, No. 2, pp. 503–506, 1983.

"Airflow Perturbation Device for Measuring Airways Resistance of Humans and Animals", Johnson et al *IEEE Transactions on Biomedical Engineering*, vol. BME–31, No. 9, Sep. 1984, pp. 622–626.

"Measurement of Alveolar Pressure in Closed–Chest Dogs During Flow Interruption", Bates et al, *The American Physiological Society*, 1989, pp. 488–492.

"A Theoretical Analysis of Interrupter Technique for Measuring Respiratory Mechanics", Bates et al, *The American Physiological Society*, 1988, pp. 2204–2214.

"Interrupter Resistance Elucidated by Alveolar Pressure Measurement in Open–Chest Normal Dogs", Bates et al, *The American Physiological Society*, 1988, pp. 408–414.

"Viscoelastic Behavior of Lung and Chest Wall in Dogs Determined by Flow Interruption", Similowski et al, *The Americal Physiological Society*, 1989, pp. 2219–2229.

(List continued on next page.)

*Primary Examiner*—Robert L. Nasser
*Attorney, Agent, or Firm*—Arent Fox Kintner Plotkin & Kahn PLLC

[57] ABSTRACT

An airflow perturbation device and system wherein airflow of a subject is alternatingly blocked and unblocked by a mechanism to provide an output of an airflow/differential pressure conversion device based on oscillating differential pressure signals created by the alternating perturbation. The signals are provided by pressure transducers which provide signals to a data acquisition computer which calculates respiratory resistance as an indicator of airway resistance. An airflow perturbation device according to the invention could be a self-contained unit wherein the airflow perturbation mechanism, differential pressure conversion device, transducers, and data acquisition computer are in a single unit. In another embodiment, an airflow perturbation device could include the airflow perturbation mechanism and pressure transducers in a single unit, and provide transducer output to the data acquisition computer for calculation of respiratory resistance.

26 Claims, 15 Drawing Sheets

OTHER PUBLICATIONS

"Stochastic Model of the Pulmonary Airway Tree and its Implications for Bonchial Responsiveness", Bates, *The American Physiological Society*, 1993, pp. 2493–2499.

"Analysis of the Behavior of the Respiratory System with Constant Inspiratory Flow", Bates et al, *The American Physiological Society*, 1985, pp. 1840–1848.

"Respiratory Resistance with Histamine Challenge by Single–Breath and Forced Oscillation Methods", Bates et al, *The American Physiological Society*, 1986, pp. 873–880.

"A Nonlinear Viscoelastic Model of Lung Tissue Mechanics", Suki et al, *The American Physiological Society*, 1991, pp. 826–833.

"Forced Oscillation Technique vs. Spirometry to Assess Bronchodilatation in Patients with Asthma and COPD", Zerah et al, *Chest*, vol. 108, No. 1, Jul. 1995, pp. 41–47.

"Measurement of Lung Function in Awake 2–4–Year–Old Asthmatic Children During Methacholine Challenge and Acute Asthma: A Comparison of the Impulse Oscillation Technique, the Interrupter Technique, and Transcutaneous Measurement of Oxygen Versus Whole–Body Plethysmography", Klug et al, *Pediatric Pulmonology* vol. 21, 1996, pp. 290–300.

"Comparative Sensitivity of Four Methods for Measuring Changes in Respiratory Flow Resistance in Man", Frank et al, *Journal of Applied Physiology*, vol. 31, No. 6, Dec. 1971, pp. 934–938.

"Lung Impedance in Healthy Humans Measured by Forced Oscillations from 0.01 to 0.1 Hz", Suki et al, *The American Physiological Society*, 1989, pp. 1623–1629.

"Normal Values of Total Respiratory Resistance and Reactance Determined by Forced Oscillations", Làndsér et al, *Chest*, vol. 81, No. 5, May 1982, pp. 586–591.

"Impedance and Relative Displacements of Relaxed Chest Wall up to 4 Hz", Barnas et al, *The American Physiological Society*, 1987, pp. 71–81.

"Mechanical Properties of Lungs and Chest Wall During Spontaneous Breathing", Nagels et al, *The American Physiological Society*, 1980, pp. 408–416.

"Pulmonary Mechanics by Spectral Analysis of Forced Random Noise", Michaelson et al, *The Journal of Clinical Investigation*, vol. 56, Nov. 1975, pp. 1210–1214.

"Respiratory Impedance by Discrete Frequency of Broadband Input Signals", Jackson et al, *Eur Rspir Rev* 1991, 1, Rev. 3, pp. 174–177.

"Evaluation of the Forced Oscillation Technique for the Determination of Resistance to Breathing", Fisher et al, *The Journal of Clinical Investigation*, vol. 47, 1968, pp. 2045–2057.

"A Simplified Measurement of Respiratory Resistance by Forced Oscillation", Goldman et al, *Journal of Applied Physiology*, vol. 28, No. 1, Jan. 1970, pp. 113–116.

"Influence of Bifurcations on Forced Oscillations in an Airway Model", Bunk et al, *Journal of Biomechanical Engineering—Transactions on the ASME*, vol. 114, May 1992, pp. 216–221.

"Influence of Waveform and Analysis Technique on Lung and Chest Wall Properties", Barnas et al, Elsevier, *Respiration Physiology*, vol. 96, 1994, pp. 331–344.

"Multi–frequency Forced Oscillation Measurement of Airway Resistance Including the Associated Phase Angle", Simm, *Pneumologie* 43, 1989, pp. 376–381.

"Test Report on the Multi–Frequency Forced Oscillation Technique with the Custo Vit", Glaser et al, *Pneumologie* 43, 1989, pp. 369–375.

"Modeling of Low–Frequency Pulmonary Impedance in Dogs", Hantos et al, *The American Physiological Society*, 1990, pp. 849–860.

"Low–Frequency Respiratory System Resistance in the Normal Dog During Mechanical Ventilation", Sato et al, *The American Physiological Society*, 1991, pp. 1536–1543.

"A Pulmonary Function Test Requiring Only Normal Breathing", Sobol, *Clinical Medicine*, Feb. 1974, pp. 19–22.

"Clinical Experience with a New Test of Pulmonary Function", Sobol, *Chest*, vol. 60, No. 2, Aug. 1971, pp. 137–140.

"An Additive Method for Airway Resistance Measurement", Kureš, *Acta Pædiatr. Scand* vol. 63, 1974, pp. 351–356.

"An Additive Method for Airway Resistance During Quiet Breathing", *American Review of Respiratory Disease*, vol. 102, 1970, pp. 970–974.

"A New Method for Measurement of Respiratory Resistance", Shaw et al, *J. Appl. Physiology:* Respirat. Environ. Exercise Physiol. 54(2), 1983, pp. 594–597.

"Forced Perturbation of Respiratory System", Schmid–Schoenbein et al, *Annals of Biomedical Engineering* vo.6, 1978, pp. 194–211.

"Frequency Dependence of Specific Airway Resistance in a Commercialized Plethysmograph", Peslin et al, *Eur Respir J.* vol. 9, 1996, pp. 1747–1750.

"Dynamic Properties of Body Plethysmographs and Effects on Physiological Parameters", John et al, *The American Physiological Society*, 1994, pp. 152–159.

"Was it Just our Problem, or Yours Too? Errors in Body Plethysmography, in Infants, Children, and Adults", Stănescu, *Pediatric Pulmonology*, vol. 11, 1991, pp. 285–288.

"Measurement of Airway Resistance with a Volume Displacement Body Plethysmograph", Jaeger et al, *J. Appl. Physiol.* 19(4), 1964, pp. 813–820.

"Variability, Reproducibility and Observer Difference of Body Plethysmographic Measurements", Teculescu et al, *Clinical Physiology* vol. 2, 1982, pp. 127–138.

"A New Method for Measuring Airway Resistance in Man Using a Body Plethysmograph: Values in Normal Subjects and in Patients with Respiratory Disease", DuBois et al, From the Department of Physiology and Pharmacology, Graduate School of Medicine, University of Pennsylvania, Philadelphia, PA, Dec. 1955, pp. 327–335.

"Effect of the Cheeks and the Compliance of Alveolar Gas on the Measurement of Respiratory Variables", Jaeger, *Respiration Physiology* vol. 47, 1982, Elsevier Biomedical Press, pp. 325–340.

AIRFLOW PERTURBATION DEVICE AND METHOD FOR MEASURING RESPIRATORY RESISTANCE

BACKGROUND OF THE INVENTION

1. Field of the Invention

The present invention is directed to a device, method, and system for measuring respiratory resistance of living organisms, in particular human beings. Respiratory resistance is a measurement which has significant clinical and physiological interest. Increased resistance can typically be related to an assortment of respiratory diseases such as asthma, bronchitis, pneumonia, emphysema, and various other obstructive disorders. Resistance measurements can be useful for evaluating the respiratory effects of bronchoconstrictive and bronchodilatory drugs, as well as airborne contaminants and natural particulates. Energy expenditure for respiratory functions can constitute a significant part of a body's total expenditure during exercise. Energy expenditure is increased when protective masks are worn, which is common in occupations wherein exposure to contaminated environments can occur. Respiratory resistance measurement, therefore, is an important measurement for many different purposes. The invention is directed to a respiratory resistance measuring device which is reasonably inexpensive, easy to use, and accurate.

2. Description of the Related Art

Several techniques are available to measure various aspects of respiratory resistance. Among those which are non-invasive, the technique of forced oscillation measures total respiratory resistance, but it requires a great deal of expertise and subject cooperation. Whole-body plethysmography measures the resistance of the airways alone, but it requires a large apparatus that is not portable or easy to use. Both techniques are quite expensive. Other techniques are invasive. A measurement of pressure that can be used to calculate part of respiratory resistance is made by the insertion of an esophageal catheter directly into the subject. These conventional measurement techniques are not appropriate for important groups of patients such as neonates, pre-school children, and the critically ill.

Airflow perturbation techniques were proposed by several groups in the 1970s as a more simple way of obtaining respiratory resistance. Dr. Arthur Johnson's interest in measuring airways resistance led him to design the first Airflow Perturbation Device (APD) in 1974, which is discussed in U.S. Pat. No. 4,220,161, which is hereby incorporated by reference. The APD was intended to be a simple, economical, non-invasive device for the measurement of airway resistance, as discussed in Johnson and Lin, *Airflow Resistance of Conscious Boars*, Transactions of the ASAE, volume 26, pages 1150–1152, 1983. This and other earlier work has produced measurements in the expected range for test subject airway resistance, but further conclusions have not been drawn. Airway resistance measurements are discussed in U.S. Pat. No. 4,856,532, the contents of which is hereby incorporated by reference. The present invention is directed to an improved Airflow Perturbation Device, as well as respiratory resistance measuring system and method. The APD of the present invention measures not airway resistance but respiratory resistance, is sensitive to resistance changes, and the measurement is correlated to airway resistance.

In order to properly understand the operation of an airflow perturbation device according to the invention, a brief background regarding respiratory mechanics is helpful.

The energy required by breathing is primarily the energy used for inspiration, or inhalation. Expiration, or exhalation, is usually a passive process driven by the elastic recoiling of the lungs and chest wall. The work of inspiration has three fractions. Work is done to overcome compliance, resistance, and inertance impedances. Compliance work expands the lungs and the enclosing chest cage against their elastic forces. Resistance work is done to overcome the viscous and frictional resistance to air flow and tissue movement. The measurement of this resistance is the primary goal of the APD. Inertance work accelerates the mass of the volume of air inhaled, the lung tissue and chest wall.

During normal quiet breathing, most of the work done is the compliance work needed to expand the lungs. A smaller amount is lost in overcoming tissue resistance. A similar amount of energy is lost to airways resistance. Mass inertia work is considered negligible, as shown in FIG. 1. During heavy breathing, such as during exercise, air must flow through respiratory passageways at a much higher velocity. The energy dissipated by airways resistance then becomes the greatest proportion of respiratory work.

These terms of compliance, resistance, and inertance are completely analogous to the electrical terms of capacitance, resistance, and inductance. This allows the use of electrical symbols in illustrating models of the respiratory system. FIG. 2 shows a respiratory model in terms of electrical components of the system made up of airways, lung tissue, and chest wall fractions.

A pressure balance equation of this model where the ground point is atmospheric pressure produces equation 1.

$$(p_{mo}-p_{atm})+(p_{alv}-p_m)+(p_{pl}-p_{alv})+(p_{mus}-p_{pl})+(p_{atm}-p_{mus})=0 \quad (1)$$

In this formula, $p_{mo}$ is mouth pressure, $p_{atm}$ is atmospheric pressure, $p_{alv}$ is alveolar pressure, $p_{pl}$ is pleural pressure, $p_{mus}$ is muscle pressure. The mouth-atmosphere term is nonzero when wearing a mask, breathing through a tube, or breathing through any other obstruction. The APD functions by periodically increasing this term. Pleural pressure is at the lung-chest wall interface. Alveolar pressure is at the air-lung tissue interface. Muscle pressure is exerted by the diaphragm.

The pressure differences between mouth, alveolar, pleural and muscle levels can be expressed by the equation for a linear circuit.

$$\Delta P = \frac{V}{C} + RV' + IV'' \quad (2)$$

where

| | |
|---|---|
| ΔP: Pressure Difference | V: Volume |
| C: Compliance | V': Flowrate |
| R: Resistance | V'': Volume acceleration |
| I: Inertance | |

The complexity of FIG. 2 can be reduced to the model shown in FIG. 3. Resistance and inertance in this model are the sums of airways, lung tissue, and chest wall components. Compliance is shown as a function of lung tissue and chest wall compliances. Airways compliance is nearly zero, so it is neglected.

Rohrer's relationship has been generalized to include different lung volumes.

$$R = K_1 + K_2 V' + \frac{K_3}{V - V_{res}} \quad (3)$$

where

| | |
|---|---|
| R: Airway resistance | V: Lung volume |
| $K_1$: First coefficient | V': Flowrate |
| $K_2$: Second coefficient | $V_{res}$: Lung residual volume |
| $K_3$: Third coefficient | |

The last fifteen years has seen much work to document the characteristic frequency dependence of respiratory resistance. While airway resistance is not highly frequency dependent at low frequencies, total respiratory resistance is. In healthy humans, respiratory resistance is relatively constant from 3 to 10 Hz. It increases at lower and at higher frequencies. More discussion of frequency dependence will follow, along with the topic of forced oscillation of the respiratory system.

If inertance and compliance are negligible, resistance equals pressure divided by flowrate. Respiratory airflow is easy to measure. Almost any human subject can breathe through a flowmeter. Pressures inside the body are much more difficult to measure, complicating the measurement of resistance. Airway resistance is that between the mouth and the alveoli. Pulmonary resistance is airway resistance plus lung tissue resistance. Respiratory resistance is pulmonary resistance plus chest wall resistance. If inertance and compliance are considerable, pressure divided by flowrate is defined as impedance. The portion of impedance consisting of inertance plus compliance is termed reactance.

Five methods have been used to measure various aspects of respiratory resistance or impedance. They are the esophageal balloon, body plethysmograph, forced oscillation technique, flow interrupter, and APD. Their abilities and limitations vary.

The esophageal balloon method, which measures pulmonary resistance, is the most direct measurement of the five. A balloon-tipped catheter is inserted through the nose down to the lower third of the esophagus. The pressure at the catheter tip is assumed to equal pleural pressure, or the pressure just outside the lung tissue. Pressure difference is measured between the catheter tip and the subject's mouth. The directness of this measurement makes it useful for validating other methods of resistance measurement. Its invasive nature limits its clinical use.

The interrupter method was one of the earliest attempts to non-invasively measure airways resistance. Neergaard and Wirz first used airflow interruption in 1927. With this method, airflow is suddenly halted and mouth pressure is monitored. The mouth pressure measured immediately upon interruption is assumed to equal alveolar pressure just prior to the interruption. It is divided by the airflow rate just prior to the interruption to produce airway resistance. This assumption is not completely valid. It neglects the effects of air mass inertance, airways compliance, and frequency dependent lung tissue viscoelastic parameters. Theoretical analysis has also suggested that upper airways compliance may cause the interrupter to underestimate resistance. Experimental interrupter data has been obtained from open-chested dogs, or dogs who have had the breastplate surgically moved to allow direct measurement. It has shown the interrupter to measure airways resistance and not pulmonary resistance. Experimental data obtained with closed-chested dogs indicates that the measurement is airways plus chest wall resistance. A compact, portable interruption device suitable for clinical use has been developed and tested against the body plethysmograph in adult human subjects. It has been shown to produce measurements correlated to, but larger than, the plethysmograph. It has also measured resistance changes from bronchodilator treatment similar to those measured by plethysmography.

DuBois introduced whole-body plethysmography for measuring airways resistance in 1956. His constant-volume plethysmograph, or body box, is a sealed container in which the subject sits and breathes. The plethysmograph had been previously used to measure thoracic gas volume by application of Boyle's Law. During exhalation, alveolar pressure exceeds box pressure as the lungs expel air through the airways. Since the box is sealed, air compression inside the lungs results in lower air pressure throughout the remainder of the box. During inhalation, air expansion inside the lungs results in greater air pressure throughout the rest of the box. Box pressure, inversely proportional to lung pressure, is monitored by a sensitive pressure transducer. Lung pressure can be measured by occluding the airflow and measuring mouth pressure. In this static system, mouth pressure and alveolar pressure are the same. Therefore, the conversion factor between box pressure and alveolar pressure is the slope of the mouth pressure-box pressure curve.

The classic DuBois airways resistance test begins with shallow panting through a pneumotach flowmeter. The technician waits for air flowrates between −0.5 and +0.5 L/s. After several seconds of box pressure-airflow data collection, a shutter closes to occlude airflow and several seconds of box pressure-mouth pressure data is collected. The conversion factor from the occlusion data is applied to the box pressures in the panting data to produce what is believed to be an alveolar pressure-flowrate curve. The slope of that curve is plethysmographic airways resistance.

Sealing a human subject inside a plethysmograph poses a thermal problem. Body heat production heats and compresses the air, so boxes are built with slow leaks or ventilation valves to release the pressure. The error caused by slowly building pressure, a low frequency signal, is minimized by performing the test with panting, a high frequency signal. An alternative instrument less sensitive to this thermic error is the volume displacement plethysmograph. It works similarly to the constant-volume plethysmograph, except that changes in box volume are monitored instead of changes in box pressures. This less-common plethysmograph is more mechanically complex and suffers a more limited frequency response.

Another problem, recognized by DuBois, is that the air volume exhaled through the pneumotach can be different than the volume inhaled due to heating, humidification, and to a much lesser degree, respiratory gas exchange. Several solutions to the heating and humidification problem have been attempted. DuBois suggested that the shallow panting minimizes this problem because the inhaled air will be pneumotach dead space air, already warm and moist. A relationship between panting frequency and plethysmographic airways resistance has been found by numerous researchers and attributed to the noninstantaneous air heating and wetting. Lower frequency panting results in lower airway resistance values. For accurate measurements at frequencies below 2 Hz, the subject can breathe air already conditioned to body temperature and saturated. Some boxes are equipped with rubber bags to hold warm, saturated air, but cost and sanitary considerations limit their use. Another alternative to deal with this problem is to mathematically remove this effect. A body box has been marketed with "Electronic BTPS correction," but this technique has been found to be inaccurate.

Body plethysmographs have found use among scientists and clinicians. Among other things, they have been used to measure the pressure-volume-flow characteristics of the lungs, test the effectiveness of bronchodilators, respiratory responses to temperature and humidity, and bronchoconstriction due to smoking. Yet this technique suffers from high technician variability and poor reproducibility. In the case of high-resistance subjects, researchers have found consistent underestimations of airways resistance. The assumption that mouth pressure equals alveolar pressure during occlusion generally holds in healthy patients. In patients experiencing spontaneous or induced bronchoconstriction, however, significant mouth-alveolar flows cause a pressure gradient. This results in a high thoracic gas volume and low airways resistance measurement.

The forced oscillation technique (FOT) was also introduced by DuBois as a way to measure respiratory resistance, the sum of airways, lung tissue, and chest wall resistances. A piston pump was used to apply sinusoidal pressure oscillations at the mouth. The pressure oscillations were compared to the resulting flow oscillations to obtain magnitude ($|Z_{rs}|$) and phase angle ($\theta_{rs}$) of the respiratory system. Flow led pressure ($\theta_{rs}$ was negative) at low frequencies indicating a prominent compliance effect. Near 6 Hz, pressure and flow were in-phase and $|Z_{rs}|$ reached its minimum value where it represented respiratory resistance alone. From this, 6 Hz is considered the resonant frequency of the average respiratory system. Pressure led flow ($\theta_{rs}$ was positive) at higher frequencies indicating a prominent inertial effect. Oscillations were induced from 2 to 15 Hz. Impedances at resonant frequencies were found to range from 2 to 4 $cmH_2O/L/s$.

Since this initial work, many researchers have modified the FOT to make the calculations easier or the measurements more enlightening. Goldman et al. (1970) measured respiratory resistance at frequencies other than at the resonant frequency with an alternative technique. With sinusoidal forcing, there are two instants per cycle when flow acceleration is zero and volumes are identical. These are at the extremes of flow. Respiratory resistance was calculated as the change in pressure between these points divided by the change in flow rate. Resistances in six healthy subjects were found to range from 1.7 to 2.5 $cmH_2O/L/s$. While these early measurements with FOT were limited to discrete frequencies, some researchers felt that additional information about the respiratory system could be gained by oscillating with a wide range of frequencies simultaneously. The development of the fast Fourier transform (FFT) for microcomputers in the 1970's enabled FOT to measure impedance in the frequency domain. The FFT of mouth pressure is divided by the FFT of flowrate to produce impedance as a function of frequency. A polyfrequent forcing function, either designed or random, is applied with a loudspeaker or piston pump. Impedances are now typically reported as having a real component and an imaginary component. The real component represents the resistance, or the in-phase component. The imaginary component represents reactance, or the out-of-phase component. Reactance is the sum of inertance and compliance impedances. No consistent differences have been found between impedances derived from discrete frequency or from broadband input frequencies ranging from 4 to 256 Hz.

Researchers usually calculate FOT resistance at relatively high frequencies in order to avoid the low frequencies associated with normal breathing. Some measurements are also taken at low frequencies, but they require a higher degree of subject cooperation. Subjects must be trained to maintain voluntary apnea for periods of approximately 30 seconds.

In healthy humans, respiratory resistance decreases sharply from 0 to 2–3 Hz. This decrease occurs almost entirely within the chest wall, with pulmonary resistance remaining constant. Respiratory resistance remains somewhat stable or decreases slightly from 2–5 Hz up to 20 Hz. Measurements conducted from 4 to 256 Hz generally indicate that respiratory resistance increases with frequency, reaching a peak near 160 Hz and then falling off at higher frequencies. Very similar results have been found in dogs. Less data exists for the effect of flowrate and volume upon the tissue resistances. It has been shown that lung tissue resistance depends upon volume. Because of these, and possibly other dependencies, resistance values must always be presented accompanied by information regarding the conditions under which they were obtained.

As with the interrupter technique, the compliance of the upper airways such as the cheeks are a concern. The dampening of the induced pressure signal here is referred to as upper airway shunting. Habib and Jackson (1993) investigated ways of reducing shunting error. FOT was implemented by applying the signal in the conventional manner, through the mouth, with the cheeks supported by the hands and also without hand support. Additionally, FOT was implemented through the mouth while the head was submerged in a rigid water tank. FOT was also implemented by applying oscillations to a rigid chamber in which the head was sealed. Standard hand cheek support was found to most closely represent shunt-free impedance.

Airflow perturbation techniques for measuring resistance were independently introduced at least four times in the 1970's. These techniques mechanically resembled the airflow interrupter but were operationally similar to the Goldman et al. (1970) implementation of FOT. Sobol (1970) introduced a device consisting of a bifurcated tube with one unobstructed flowpath and one screened flowpath. A shutter directed air alternately through either flowpath. Airways resistance was calculated from the ratio of unscreened to screened flowrates during inhalation. Flowrates were measured with a hot-wire anemometer. The calculation also required screen resistance. Both healthy subjects and respiratory patients were tested with the device. A strong correlation between the new technique and plethysmographic resistance was found, with Sobol's resistances being consistently higher.

Kures (1974) introduced a perturbation device constructed from a pneumotach with an attached shutter that could be closed to increase resistance without completely occluding flow. His "Additive Technique" calculated resistance from the ratio of the mouth pressure perturbation magnitude to the flow perturbation magnitude. Unlike Sobol's method, which required the knowledge of screen resistance, this method did not require knowledge of the shutter resistance. Healthy adults, healthy children, and asthmatic children were tested. These resistances were reported as the average of inspiratory and expiratory values. They were compared to plethysmographic resistance and found to be both correlated and of the same magnitude.

At about the same time, Johnson et al. (1974) introduced the APD as disclosed in U.S. Pat. No. 4,220,161. This device has one flowpath with a screened resistance mounted on a rotating wheel. The screened wheel provided for smooth, quick switching from substantially unperturbed to maximally perturbed flow. Resistance was calculated using the mouth pressure perturbation magnitude relative to the known screen resistance. Later, the APD resistance calculation dispensed with the use of screen resistance and calculated airway resistance as the magnitude of the mouth pressure perturbation divided by the magnitude of the flowrate perturbation. Measurements taken from healthy subjects were found to be similar in magnitude to plethysmographic resistance. Measurements taken in live pig lungs with an intraluminal catheter have shown perturbations to extend to the twelfth airway bifurcation, but not necessarily beyond. APD resistances tended to be higher in the expiratory direction than in the inspiratory direction. They tended to increase with flowrate.

Schmid-Schoenbein and Fung (1978) built a perturbation device similar in appearance to the APD but with a partially-closing shutter in place of the rotating screen. They attempted to determine not just resistance, but inertance and compliance as well, by taking multiple samples during the perturbation. Their technique involved digitally sampling about 10 points over the course of a 30 to 80 ms perturbation. Perturbations were visually selected. The three values were determined by computer as best fitting their model of expected flow drop with respect to expected pressure jump. Of the three parameters, only resistance was consistent and in the expected range. Compliance values varied greatly. Inertance values were negative and therefore incorrect.

Shaw et al. (1983) were the most recent to reintroduce a perturbational device. Their device closely resembled the APD, but with a perforated metal plate sliding into the flowpath between the mouth and pneumotach rather than a screen open segment rotating beyond the pneumotach. Resistance was calculated from the magnitude of the flow perturbation with respect to the resistance of the perforated plate. Healthy subjects and COPD patients were tested. Resistance values were found to match plethysmographic resistance. Resistance measurements were found to vary with the number of holes in the perforated plate. Paradoxically, the healthy subjects used to demonstrate how the measurement changed with hole count all had higher resistances than the healthy subjects used to correlate perturbational resistance to plethysmographic resistance.

The literature is not consistent in its definition of perturbational resistance. Some authors treat the effective origin of the pressure driving respiration as the alveoli and assume that the perturbation does not extend through tissue. Therefore, perturbational resistance is airways resistance. They have reported generally lower resistance values. The other authors state that perturbation measures total respiratory resistance. They generally report higher resistance values.

SUMMARY OF THE INVENTION

The present invention is directed to a portable airflow perturbation device which is small, lightweight, and effective for generating signals which can be used to determine respiratory resistance in a patient. The device includes a housing, and an airflow/differential pressure conversion device, such as a pneumotach, on an input side of the housing. The pneumotach or pressure conversion device has an input and an output, and a first and second pressure tap thereupon. A perturbation adjustment mechanism, such as an adjustment nut, can be provided on an input side of the housing, for adjusting a perturbation level. An alternating perturbation mechanism, such as a segmented wheel, is movably attached to the housing and is disposed at an output of the pneumotach or conversion device. The segmented wheel alternatingly blocks and unblocks the output of the airflow/differential pressure conversion device. A moving device such as an electric motor is attached to the housing for moving the segmented wheel, and first and second pressure transducers are connected to the respective first and second differential pressure taps for determining first and second differential pressures. Output signals are provided to a data acquisition system or signal processing device for determining parameters associated with the respiratory system of the patient.

A complete system according to the invention would include an airflow perturbation device as discussed above, and a data acquisition device such as a computer which acquires the signals output from the airflow perturbation device, and includes a storage means for storing a plurality of sets of data over a predetermined period of time. The data acquisition device includes processing device for calculating the lung volume, perturbation data, virtual data, and/or respiratory resistance of the patient.

A method of determining respiratory resistance according to the present invention includes the general steps of calibrating an airflow perturbation system as discussed above, then having a patient breath normally into the input of the perturbation device. The data acquisition device then samples data output by the pressure transducers, and performs a number of calculations, in order to determine respiratory resistance.

BRIEF DESCRIPTION OF THE DRAWINGS

For a proper understanding of the present invention, reference should be made to the appended drawings, wherein.

DETAILED DESCRIPTION OF THE PREFERRED EMBODIMENTS

Figure 4:
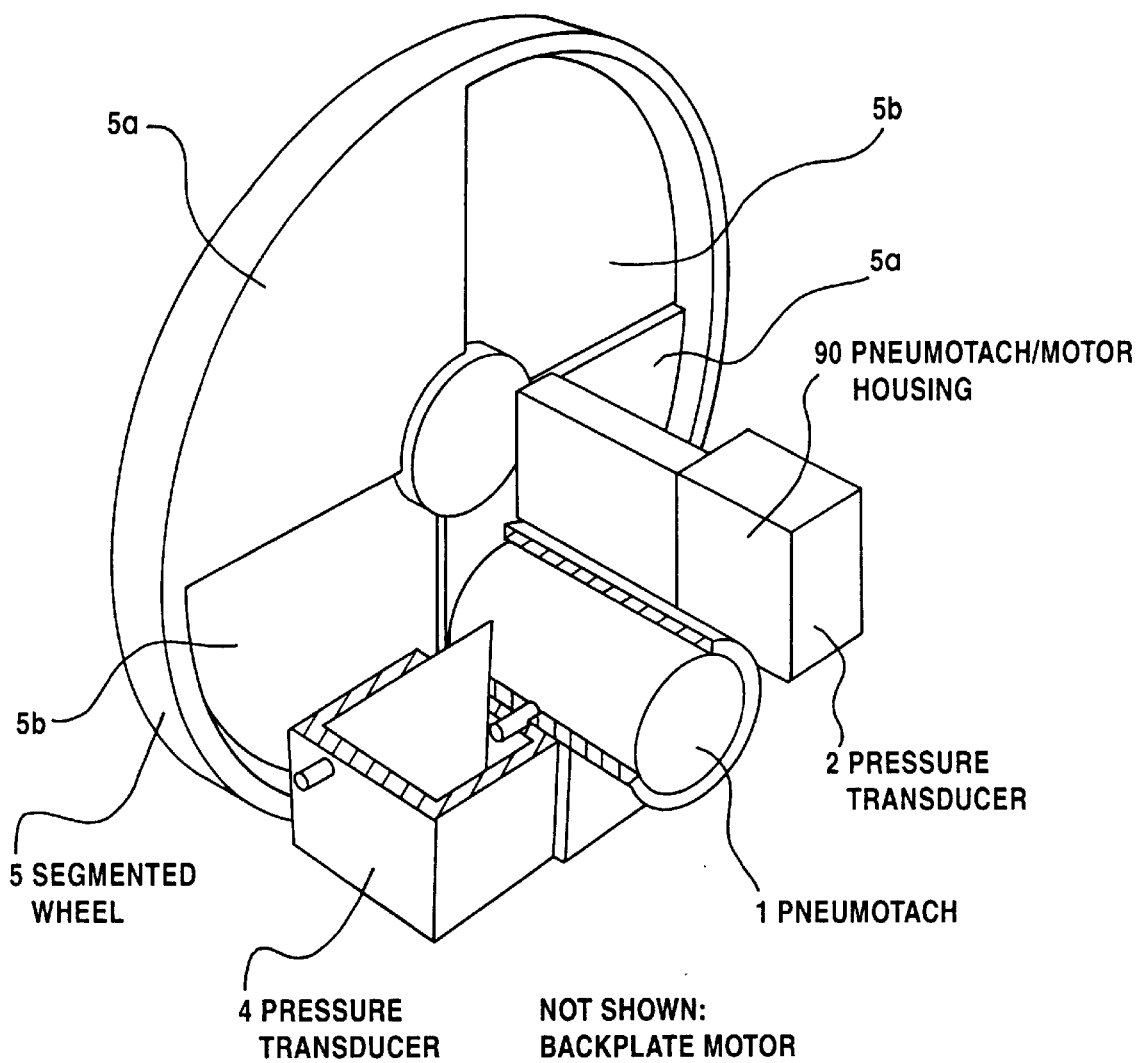
FIG. 4 illustrates a partial view of certain elements of an airflow perturbation device according to the invention.
Figure 5:
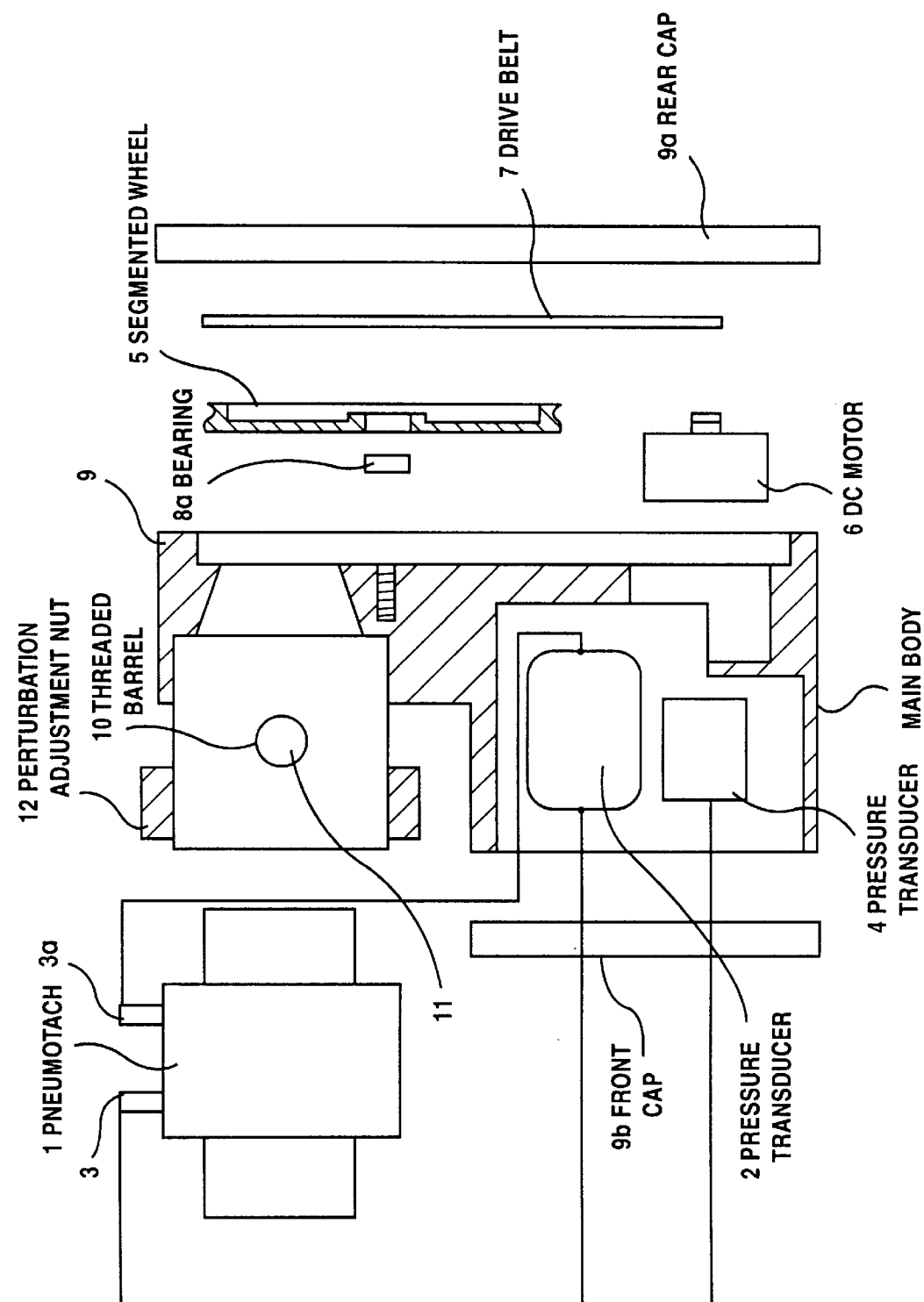
FIG. 5 illustrates a side assembly view of an embodiment of an airflow perturbation device according to the present invention.
Figure 6:
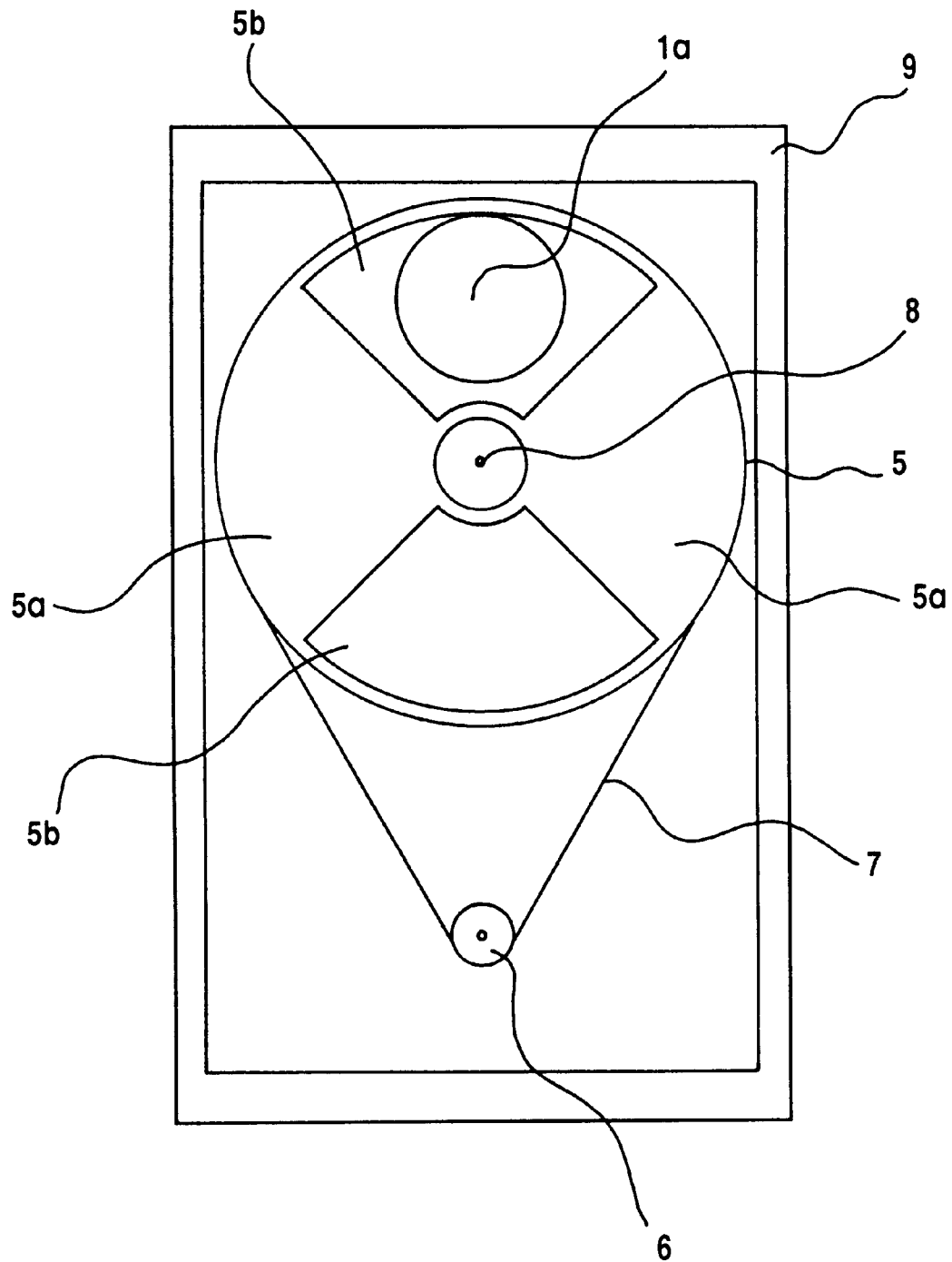
FIG. 6 illustrates another view of an APD according to FIG. 5.
Figure 7:
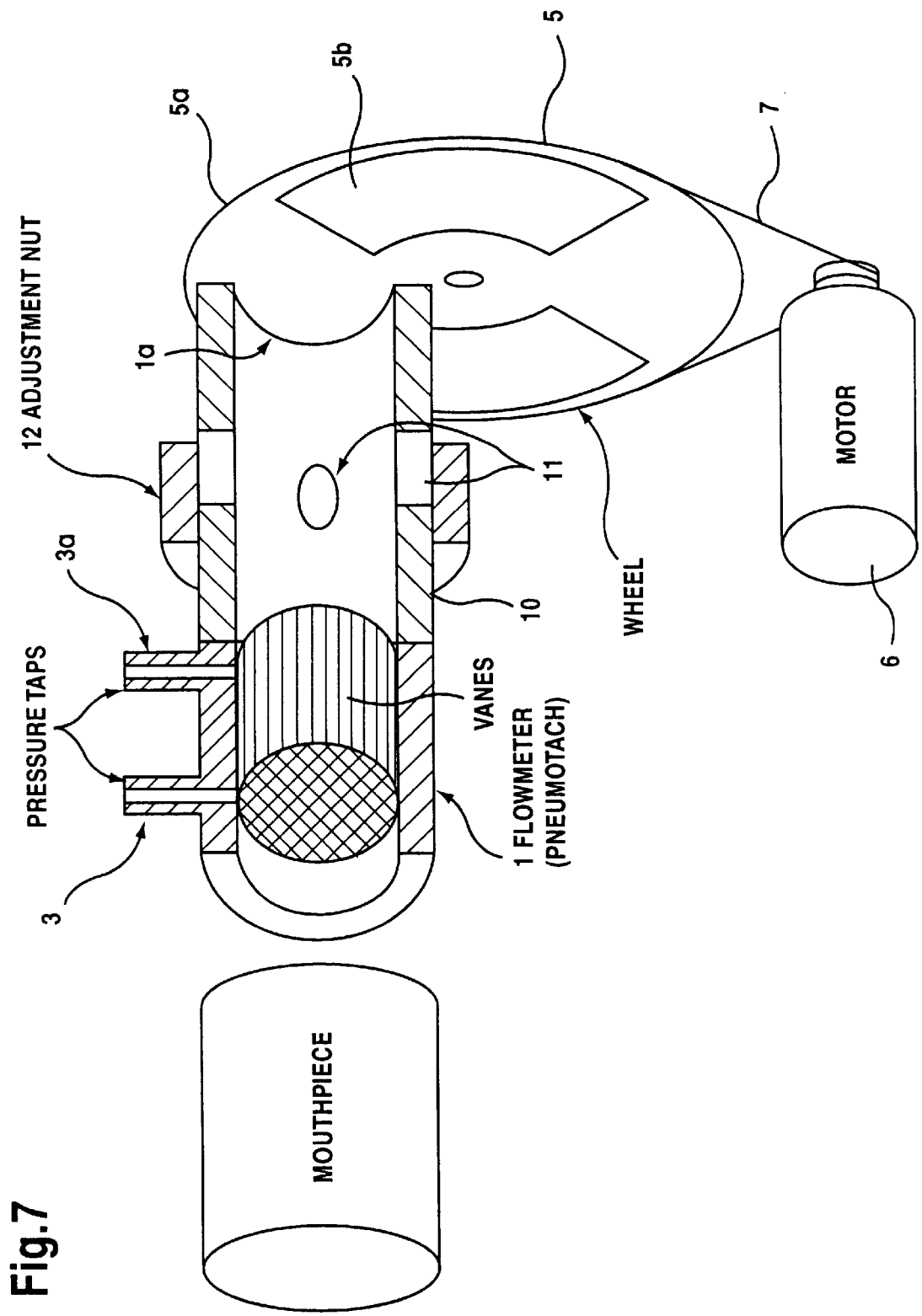
FIG. 7 illustrates certain elements of the input side of the APD of FIGS. 5 and 6.

A portable Airflow Perturbation Device (APD), small enough to fit entirely inside a padded 18×40×60 cm carrying case, was constructed. The APD consists of a perturbation mechanism, a perturbation mechanism power supply, a signal conditioning circuit housing, and a data acquisition computer. The perturbation mechanism, as shown in two different embodiments in FIGS. 4–7, is built with a pneumotach such as a Fleish #2 pneumotach, indicated as reference numeral 1. The parts are connected to a housing 90 as shown in FIG. 4, or a housing 9 as shown in FIG. 5. Two pressure taps 3 and 3a have a pressure transducer 2 connected between them, to measure flowrate. Tap 3 is also connected to a second pressure transducer 4 that measures mouth pressure relative to the atmosphere. Both transducers can be, for example, VALIDYNE (tm) model DP-15, or DATA INSTRUMENTS DCAL 401, or DCAL 420. Numerous other types of transducers are suitable. The mouth pressure transducer 4 contains, as an example, a 6.90 kPa (max.) diaphragm while the flow transducer 2 contains, also as an example, a more sensitive 0.69 kPa (max.) diaphragm. Airflow is perturbed by a segmented wheel 5 mounted perpendicular to the pneumotach flowpath. The wheel is divided into two large blocking segments 5a and two smaller, open segments 5b. The two small segments 5b, are approximately the same width as and just large enough to cover airflow opening 1a. In an optional embodiment, the larger blocking segments can be screened segments or perforated segments. Two perturbations are induced with each revolution of the wheel. The wheel may be fixed to and driven by a voltage-controlled DC electric motor 6 fitted with an appropriate gearhead providing, for example, a 41:1 gear reduction, as shown in FIG. 4. The motor and gearhead assembly provides a wheel rotation of 45 RPM per volt excitation. Alternately, motor 6 may drive segmented wheel 5 by an appropriate speed-reducing power transmission device such as a gear, chain, or belt, with speed being controlled based upon a relative size of the pulley or gear on the output shaft and the outer perimeter of the segmented wheel. Other speed control methods could be employed to provide an appropriate perturbation rate (frequency). FIGS. 5–7 illustrate drive belt 7 to rotate segmented wheel 5, with the segmented wheel rotating on shaft 8 and bearing 8a.

In the embodiment of the invention shown in FIG. 4, pneumotach 1 is disposed directly into an input side of the APD housing 90. In the second embodiment, shown in more detail in FIGS. 5–7, pneumotach 1 is inserted into threaded barrel 10, having at least one aperture 11 therein. A perturbation adjustment nut 12 is rotatably disposed on the threads of the threaded barrel. Rotation of perturbation adjustment nut 12 enables selective constriction or closure of aperture 11, thereby enabling a user of the second embodiment to adjust device resistance to provide an appropriate sensitivity based upon respiratory resistance of the subject, therefore providing a more accurate measurement. A plurality of apertures, such as four, can be provided. A partial cutaway version of the embodiment of FIGS. 5 and 6 (with a significant portion of the housing and the transducers not shown) illustrates the relationship of the pneumotach, threaded barrel 10, adjustment nut 12, as well as the vanes within the pneumotach. A mouthpiece can be attached to the input side of the pneumotach, as shown. In the embodiment of FIG. 4 without the perturbation adjustment nut and threaded barrel, a predetermined value is used to adjust device resistance to provide an approximated sensitivity. Utilizing a perturbation adjustment mechanism according to the embodiment of FIGS. 5–7, however, enables a user or technician to adjust the device resistance to provide an appropriate sensitivity based upon the respiratory resistance of the patient; the adjustment can be made by rotating the perturbation adjustment nut 12, while monitoring the relationship of device resistance to respiratory resistance using the screen of the data acquisition computer, until an appropriate sensitivity is provided, such as a flow reduction value of approximately 30%. This manual adjustment configuration can be replaced by an automatic feedback system wherein device resistance data and respiratory resistance data are input to the computer, and the computer outputs control signals to a servo or other automated adjustment mechanism. Either the manual or automated systems can be implemented so as to adjust sensitivity in real time, maximizing accuracy and speed of the measurement.

The housing 9 of the embodiment shown in FIG. 5 includes a rear cap 9a which encloses segmented wheel 5 and drive belt 7, as well as a front cap 9b, which encloses the transducer portions. The housing may utilize differing enclosure configurations.

Housing 90 of the embodiment of FIG. 4 is such that pneumotach 1 is disposed in a central portion of the housing, with pressure transducer 4 on one side of the pneumotach, and pressure transducer 2 on the other side of the pneumotach. Motor 6, not shown in FIG. 4, is disposed above the pneumotach and includes an appropriate gear reduction with segmented wheel 5 directly attached. Housing 90 can be made of any suitable material, such as metal or nylon.

The embodiment of FIGS. 5–7 is a differing configuration wherein housing 9 includes the threaded barrel 10 at an upper portion thereof, with perturbation adjustment nut 12 thereupon. Pneumotach 1 is inserted into an end of the threaded barrel. Underneath threaded barrel 10, and disposed within a cavity in housing 9, are transducers 2 and 4, which receive air pressures from pressure taps 3 and 3a. The transducers as well as the segmented wheel and drive belt are enclosed by rear end cap 9a and front end cap 9b, as discussed above.

The perturbation mechanism power supply provides, as an example, 2.5 VAC to the pneumotach heater and 9.0 VDC to the screen motor. The signal conditioning circuit housing holds a VALIDYNE (tm) CD72-2 dual demodulator, or equivalent, and a two-channel unity-gain differential amplifier. The demodulator provides excitation to the transducers and amplification of their output. Output of the CD72-2 ranges from −10 to +10V so 2:1 voltage dividers were added to avoid saturating −5 to +5V A/D converters. The +/−15 VDC power supply of the demodulator is used to power the differential amplifier. The amplifier allows additional instrumentation with floating grounds to be added to the system and referenced to a common ground, as shown in FIG. 7a. In an alternative configuration, lowpass filters could be used in conjunction with transducers having 0–5 V DC output, thereby avoiding the need for the demodulators and voltage dividers (see FIG. 7b).

A conventional portable notebook personal computer with a suitable data acquisition PCMCIA A/D card served as the data acquisition computer. Software for the APD, called APDRT, was written in the Visual Basic for Applications (VBA) macro language used with the Excel 4.0 (tm) spreadsheet application. APDRT logged pressure and flow data from the perturbation mechanism and had the ability to report resistance in real time.

Figure 1:
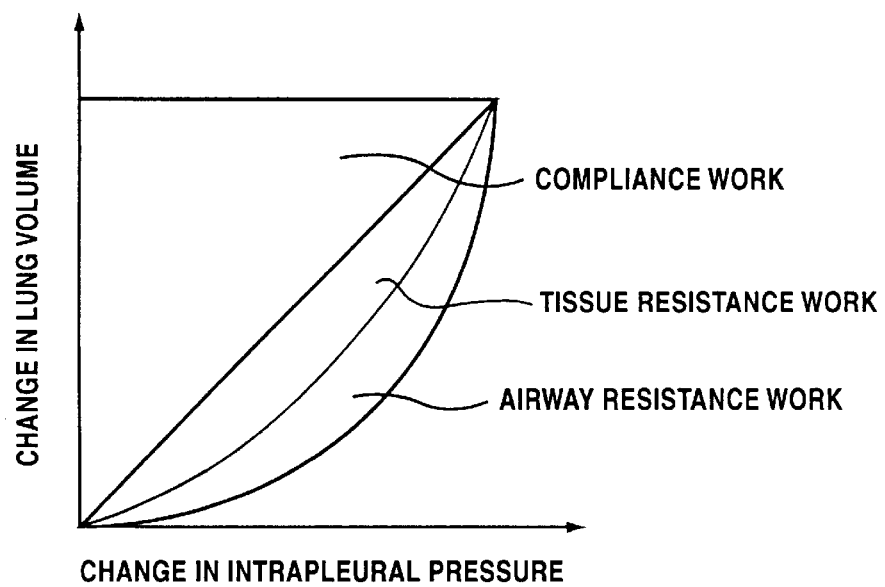
FIG. 1 illustrates the change in lung volume based upon a change in intrapleural pressure, and illustrates respiratory work.
Figure 2:
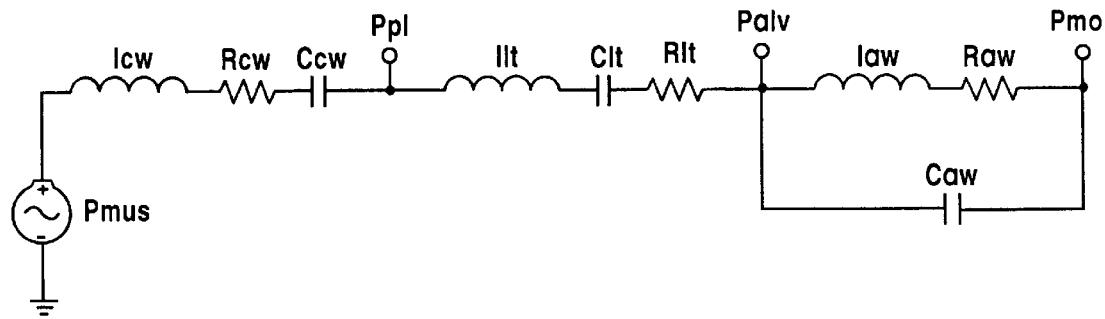
FIG. 2 illustrates a respiratory model in terms of electrical components.
Figure 3:
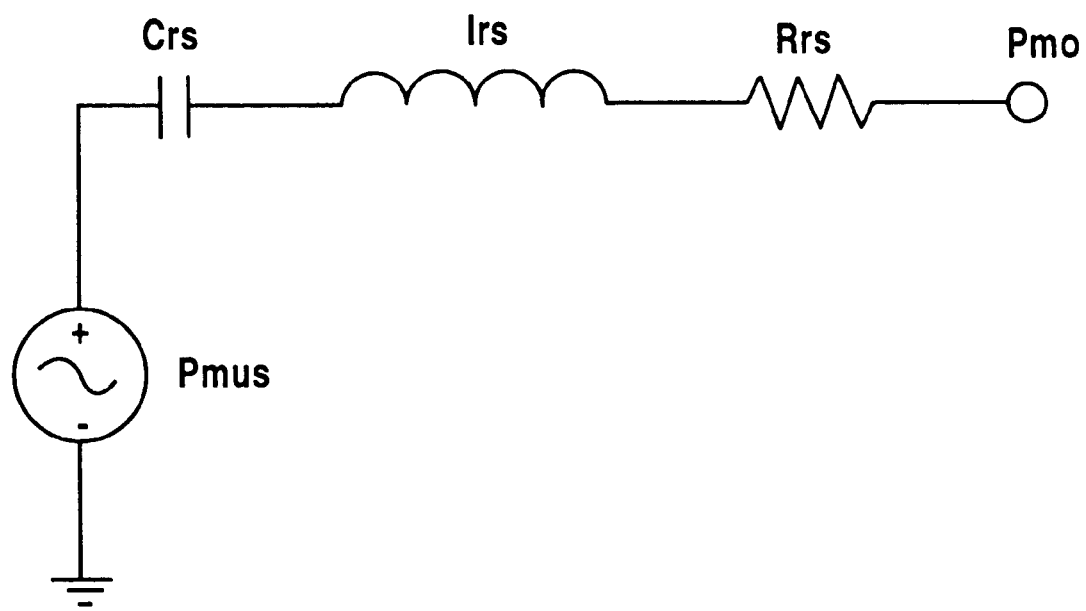
FIG. 3 illustrates a simplified or reduced version of the electrical model of FIG. 2.
Figure 8A:
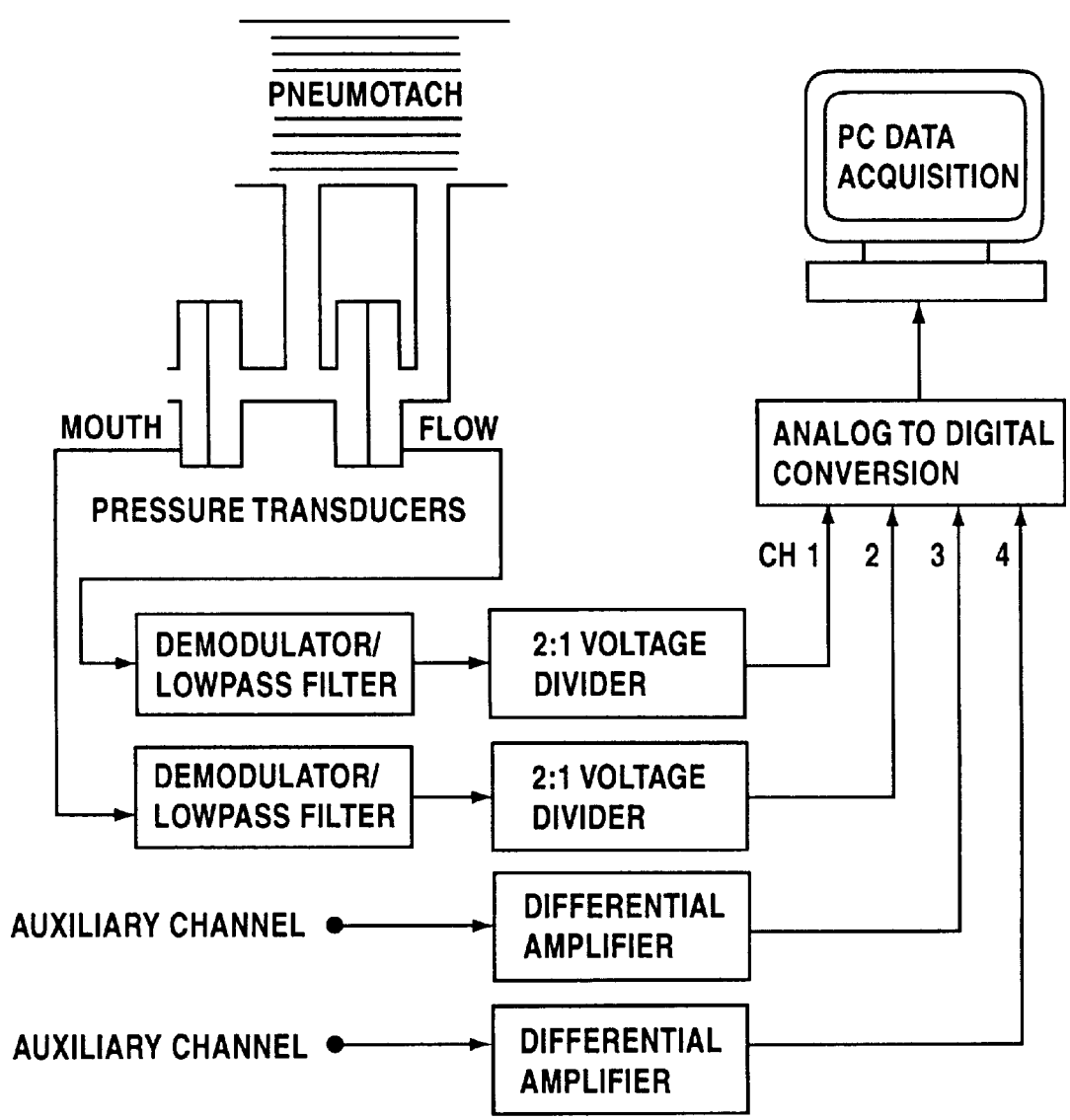
FIGS. 8a and 8b illustrate two embodiments of an APD according to the present invention being connected to a data acquisition computer.
Figure 8B:
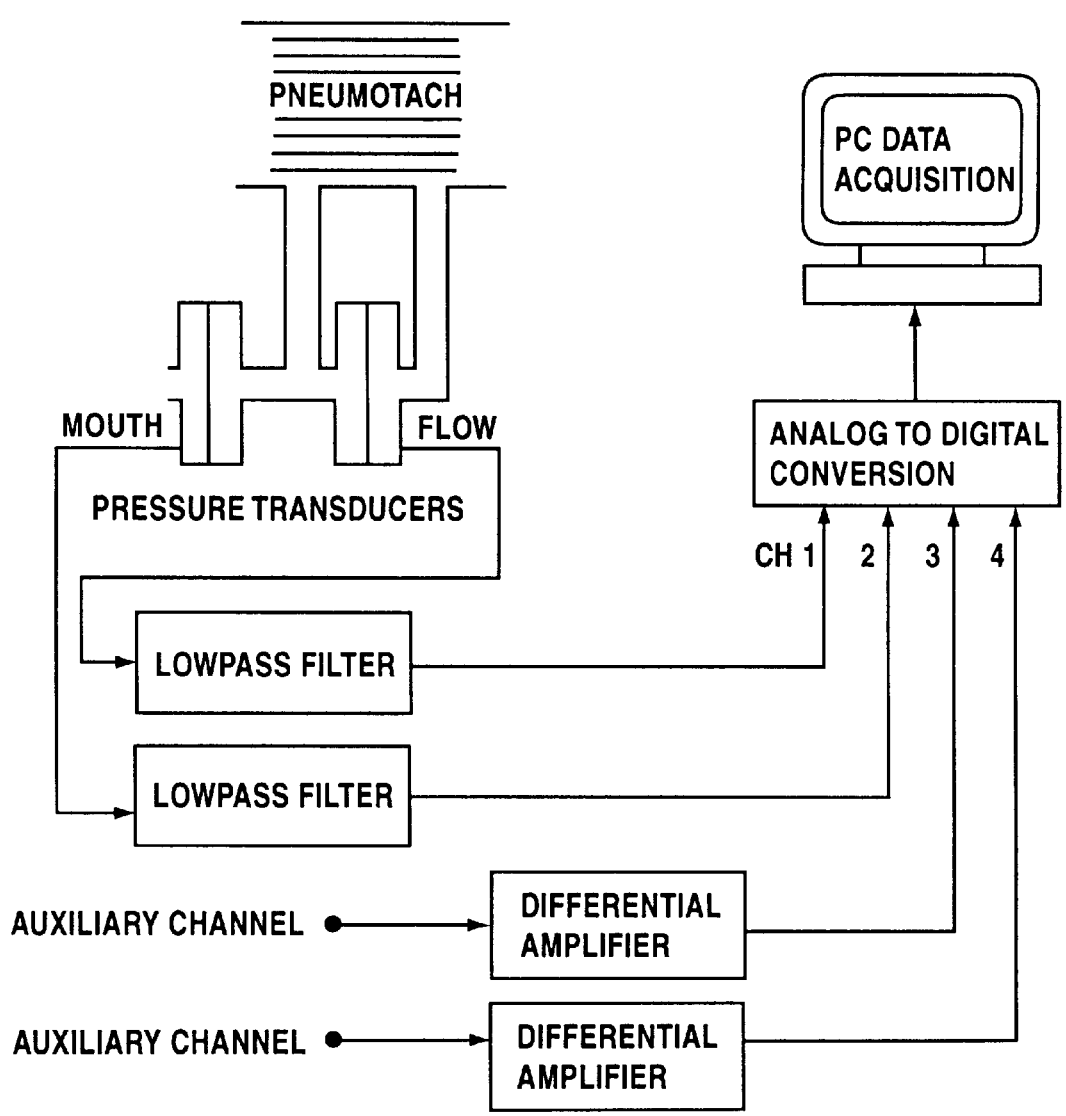

The lumped-parameter model of the respiratory system shown in FIG. 3 serves as the model for APD operation. The APD itself acts as a variable resistor. FIG. 8 represents the APD in use. The subject breathes through the device. All airflow passes through the device, represented in FIG. 9 by a resistor ($R_{dev}$).

This is a first order linear system described by the equation $$P_{mus} - P_{mo} = \frac{1}{C_{rs}} V + R_{rs} V' + I_{rs} V'' \quad (4)$$

The APD briefly perturbs the airflow to and from the respiratory system at regular intervals. Real data are those values recorded during the perturbation. Virtual data are values obtained by interpolating between pre- and post-perturbational values. At any instant during perturbation, equation 5 describes the real data and equation 6 represents virtual data.

$$P_{mus} - P_{mo1} = \frac{1}{C_{rs}} V + R_{rs} V'_1 + I_{rs} V''_1 \quad (5)$$

$$P_{mus} - P_{mo2} = \frac{1}{C_{rs}} V + R_{rs} V'_2 + I_{rs} V''_2 \quad (6)$$

Figure 9:
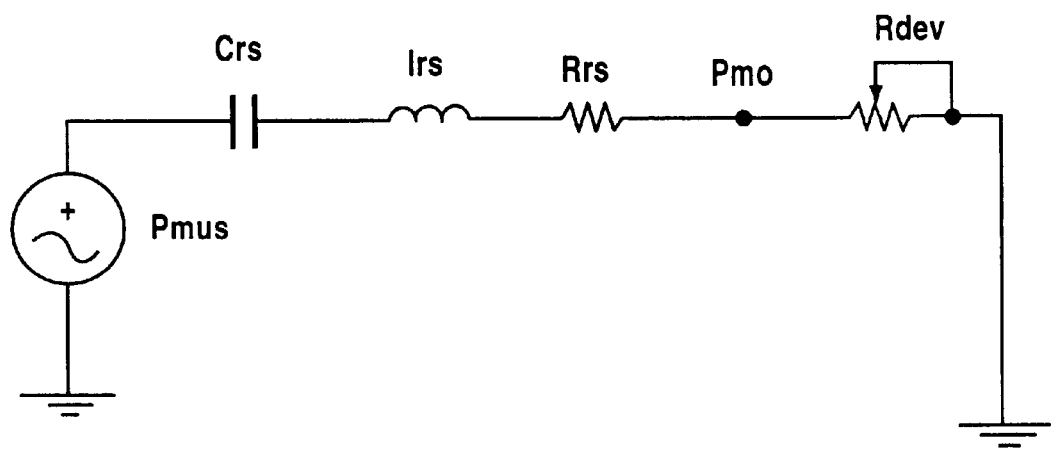
FIG. 9 illustrates an electrical model according to FIG. 3, with an APD according to the present invention used therein.

Following the model of FIG. 9, all values except V' and V" are assumed to be the same in real and virtual data. Equation 6 is subtracted from equation 5 to produce equation 7

$$P_{mo2} - P_{mo1} = R_{rs}(V'_1 - V'_2) + I_{rs} V''_1 - I_{rs} V''_2 \quad (7)$$

The contribution of pressure drop due to inertance effects are negligible during normal breathing so $I_{rs} V''_1$ can be dropped from the equation. At the instant of minimum flow rate during the perturbation, $V''_2$ is equal to zero. At that instant, equation 7 can be simplified to equation 8 or equation 9.

$$\Delta P = R_{rs} \Delta V' \quad (8)$$

$$R_{rs} = \frac{\Delta P}{\Delta V'} \quad (9)$$

where $\Delta P = P_{mo2} - P_{mo1}$: Mouth Pressure Perturbation Magnitude $\Delta V' = V'_1 - V'_2$: Flow Perturbation Magnitude Therefore, an instantaneous measurement of resistance can be taken as the ratio of the mouth pressure perturbation magnitude to the flowrate perturbation magnitude. From this point forward, this value will be denoted by the symbol $R_{apd}$.

The validity of the assumption that resistance remains constant during the perturbation is not known. Airway resistance normally varies primarily with two factors: lung volume and flowrate. Lung volume is not a problem as it is the same whether a perturbation occurs or not. The flowrate dependency of the resistance, on the other hand, may need to be dealt with. There are two ways to do this. The smallest perturbations would serve to minimize the resistance change. Unfortunately, the smallest perturbations would have the smallest signal-to-noise ratio. The alternative is to consider resistance as a function of flowrate. Equations 6 and 7 can be rewritten neglecting compliance and inertance terms, which are known to drop out, and by substituting the first two Rohrer coefficients for R.

$$P_{mus} - P_{mo1} = K_1 V'_1 + K_2 V'^2_1 \quad (10)$$

$$P_{mus} - P_{mo2} = K_1 V'_2 + K_2 V'^2_2 \quad (11)$$

Subtracting equation 11 from equation 10 yields equation 12.

$$P_{mo2} - P_{mo1} = K_1(V'_1 - V'_2) + K_2(V'^2_1 - V'^2_2) \quad (12)$$

This can be rewritten as $$P_{mo2} - P_{mo1} = K_1(V'_1 - V'_2) + K_2(V'_1 - V'_2)(V'_1 + V'_2) \quad (13)$$

Dividing through by the flowrate perturbation magnitude yields equation 14.

$$\frac{\Delta P}{\Delta V'} = K_1 + K_2(V'_1 + V'_2) \quad (14)$$

Keeping the definition of R from equation 9, equation 15 follows.

$$K_1 + K_2(V'_1 + V'_2) = R \quad (15)$$

Solving for two unknown Rohrer coefficients requires two equations. R could be evaluated at two different flowrates during a single perturbation. This would require the correct calculation of mass inertia and removal of inertance effects. While inertance effects are normally negligible, they become much larger during the sudden flow volume deceleration of perturbation. The calculated mass inertia would likely contain considerable error. Alternatively, R could be evaluated from two different perturbations. Let $V'_{1A}$ and $V'_{2A}$ be the real and virtual flowrates used in calculating resistance $R_A$ and let $V'_{1B}$ and $V'_{2B}$ be the real and virtual flowrates used in calculating resistance $R_B$. Rohrer coefficients are then obtained from equations 16 and 17.

$$K_2 = \frac{R_A - R_B}{(V'_{1A} + V'_{2A}) - (V'_{1B} + V'_{2B})} \quad (16)$$

$$K_1 = R_A - K_2(V'_{1A} + V'_{2A}) \quad (17)$$

Figure 10:
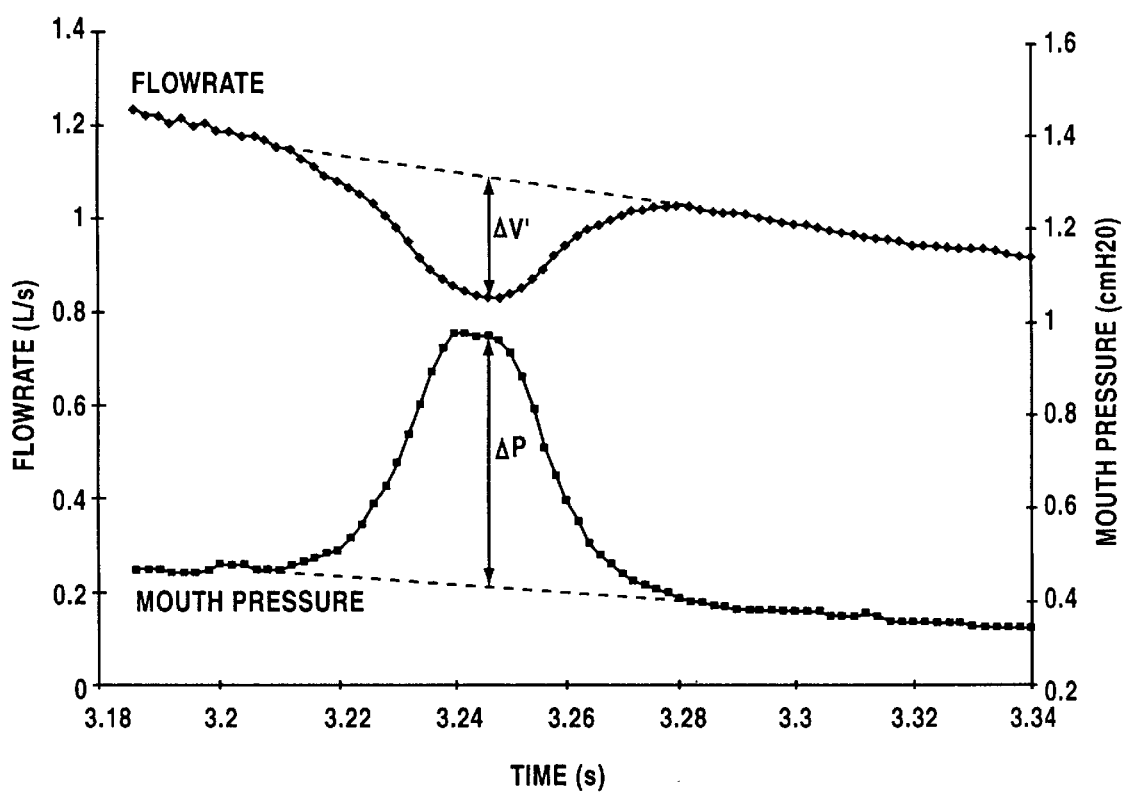
FIG. 10 illustrates a typical airflow perturbation induced by an APD of the present invention.

A typical perturbation induced by the APD can be seen in FIG. 10.

Because resistance varies with lung volume, $K_1$ and $K_2$ needs to be estimated from more than two perturbations. Taking a large sample of perturbations and finding the best-fitting Rohrer coefficients can minimize the volume variation error. According to equation 16, resistance is a linear function of flowrate. Least-square linear regressions can be determined for R as a function of $V'_1$ and R as a function of $V'_2$. These regressions can be algebraically manipulated to describe $V'_1$ and $V'_2$ as a function of R. Note that the least-square linear regressions for $V'_1$ and $V'_2$ as a function of R can be different and are not used here. Using $m_1$ and $m_2$ for slopes and $b_1$ and $b_2$ for intercepts, these regressions take the form of equation set 18.

$$V'_{1A} = m_1 R_A + b_1$$

$$V'_{2A} = m_2 R_A + b_2$$

$$V'_{1B} = m_1 R_B + b_1 \quad (18)$$

$$V'_{2B} = m_1 R_B + b_2$$

Inserting these equations into equations 16 and 17 and simplifying produce equations 19 and 20.

$$K_2 = \frac{1}{m_1 + m_2} \quad (19)$$

$$K_1 = \frac{-(b_1 + b_2)}{m_1 + m_2} \quad (20)$$

These equations allow fast determination of two Rohrer coefficients when resistance is linearly related to flowrate. In the event of constant resistance, $m_1$ and $m_2$ approach infinity and $K_2$ approaches zero. Resistance is then equal to $K_1$.

Figure 11:
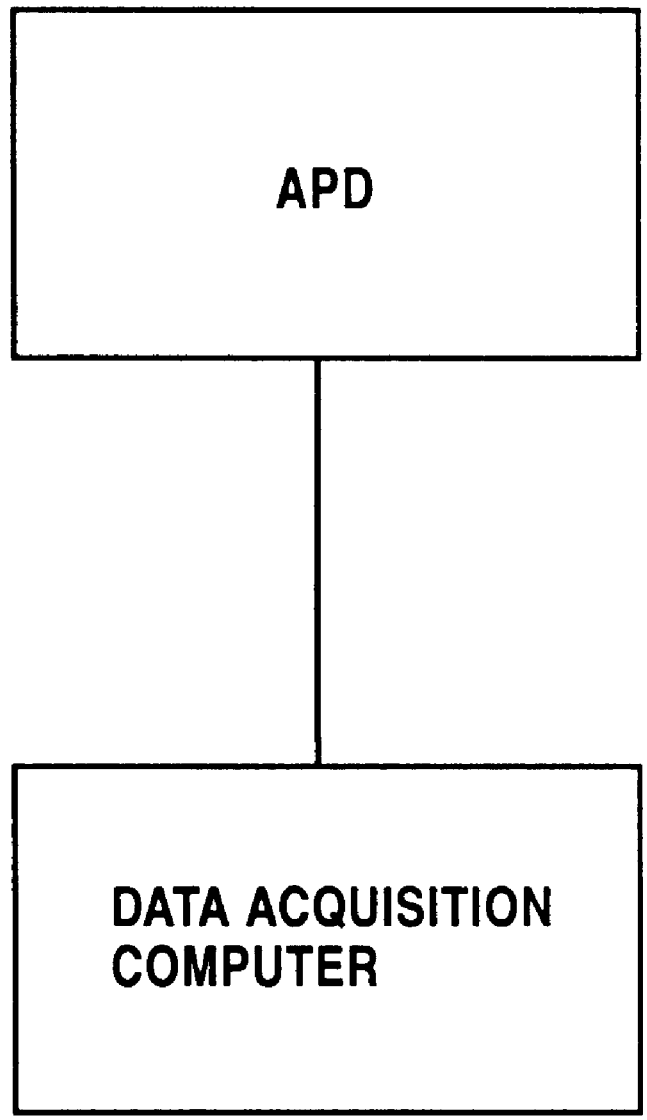
FIG. 11 is a block diagram illustrating a system according to the present invention, wherein an APD is connected to a data acquisition computer.

FIG. 11 is a block diagram which illustrates an airflow perturbation device connected to a data acquisition computer. As noted previously, the data acquisition computer comprises a conventional personal computer with an appropriate data acquisition card, running specialized software which, in the best mode of the invention, is a program referred to as APDRT. Calibration of the transducers and calculation of resistance is handled by the program.

In operation, as will be discussed below, a subject breathes normally into the input side of the device, while the perturbation mechanism, in this case the segmented wheel, is rotated at the output of the pneumotach. Perturbations are created when the open and closed segments of the wheel alternatingly pass in front of the pneumotach output, therefore effecting the differential pressure between the two pressure taps. The system is configured to determine when a perturbation begins based upon the relationship of mouth pressure to flowrate. A number of other perturbation determination methods can be implemented; the mouth pressure to flowrate determination is one embodiment. As shown in FIG. 10, an upward peak in mouth pressure and a downward peak in flowrate indicates a perturbation. The data acquisition computer then estimates mouth pressure and flowrate without a perturbation, based upon pressure flow immediately prior to and after the perturbation. This estimated or virtual data is discussed previously with respect to equations 5 and 6. Respiratory resistance is then determined based upon the difference between actual perturbation data and virtual data.

The determination of respiratory resistance according to the present invention enables the invention to determine numerous parameters which had not previously been determinable. First, relative lung volume can be determined based upon the flowrate data provided to the data acquisition computer. The data acquisition computer integrates the flowrate, as discussed previously.

The present invention also utilizes data output from the pressure transducers to separately determine inhalation resistance and exhalation resistance. Perturbations occurring during inhalation would be detected as a vacuum, and therefore have a negative value. These perturbations are stored as inhalation perturbations. Exhalation perturbations would have a positive value, and are therefore stored as exhalation perturbations. The device can therefore separately calculate respiratory resistance during inhalations and exhalations, and this data can then be used to diagnose and treat various respiratory illnesses.

The data acquisition software, referred to as APDRT, includes three macro modules containing the VBA code, one spreadsheet containing the user interface of buttons and displays, one spreadsheet of calibration values, one spreadsheet of output values, and a chart of output values. A printout of the APDRT software is attached.

The macro sheet "Dec" contains function declarations for the dynamic link library NIDAQ.DLL. These functions give APDRT access to the data acquisition card. Samples are taken alternately from two of the card's eight channels at 1 ms intervals and saved to a single array of 16 bit integers. This corresponds to a scanning frequency of 500 Hz.

The macro sheet "Cal" contains all functions associated with APD calibration. A two-point linear calibration is used with the mouth pressure transducer. The DP-15 transducers have less than 0.5% nonlinearity over their specified full scale range while the carrier demodulator has less than 0.05% nonlinearity. The two points used are atmospheric pressure and $-10.0$ $cmH_2O$ relative to atmosphere. The pneumotach is calibrated for flowrate with independent linear calibrations for exhalation and inhalation. The contents of a 3 L calibration syringe are injected and withdrawn through the pneumotach over the duration of 3 seconds in each direction. The positive pressure drop across the pneumotach is numerically integrated to get exhalation volume and the negative pressure drop is integrated to get inhalation volume. These integrals are compared with the known syringe volume to obtain calibration factors.

Functions were also written to confirm and maintain proper calibration. Transducer baseline voltage output will vary slightly with position and temperature. For example, tilting the APD after calibration can cause the weight of the internal membranes of certain types of transducers to shift the output from several millivolts positive to several millivolts negative. A "Re-Zero" function was created to record new baseline voltages from both transducers. The function reports the magnitude of the change to alert the user to possible problems. A volume measurement function, independent of the flow calibration function, was written to check flow rate calibration. The user provides the flow of a known volume through the pneumotach. The function integrates the flow rate and reports volume change. Flow is recalibrated if volume verification error exceeds 2.5%.

Figure 12:
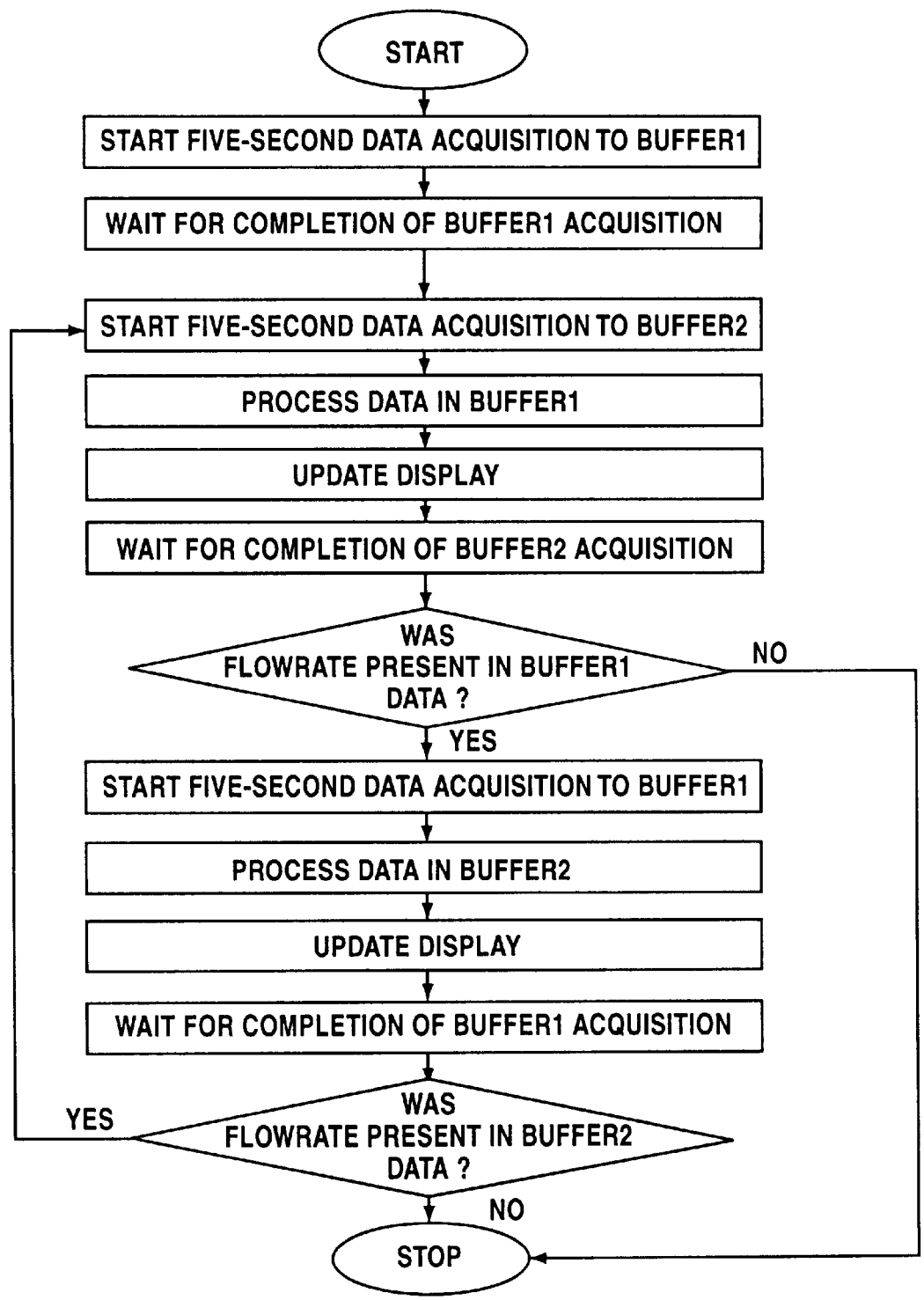
FIG. 12 is a flowchart illustrating the process of data acquisition and processing according to the present invention.

The macro sheet "Main" contains the functions that collect pressure and flow data and calculated resistance. One function collects data for five seconds, while another collects data continuously until flow through the APD terminates. After the five-second data collection period, resistance is calculated from each perturbation. A function is available to then save and plot all of the raw data from the five seconds to a new spreadsheet. Another function is available to save and plot raw data from just the last perturbation detected. The continuous acquisition function logs data in five second segments to two separate buffers. When the first buffer is full, acquisition switches to the second buffer. While the second fills, data from the first buffer is processed. If no perturbations are detected, a flag is set to end acquisition. The average of the last ten inhalation and the last ten exhalation resistance measurements is displayed onscreen. After processing of the data from the first buffer, the progress of the acquisition to the second buffer is checked. When the second buffer is full, acquisition switches back to the first buffer while the second buffer is processed. The flowchart of FIG. 12 illustrates this process.

Figure 13A:
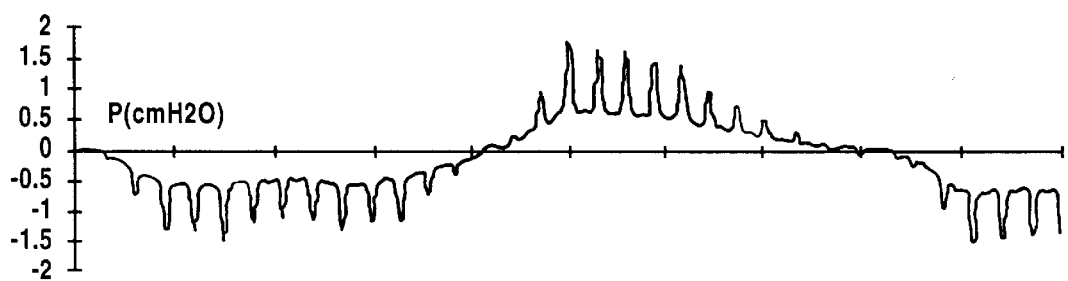
FIGS. 13a–13d illustrate typical acquisitions according to the present invention.
Figure 13B:
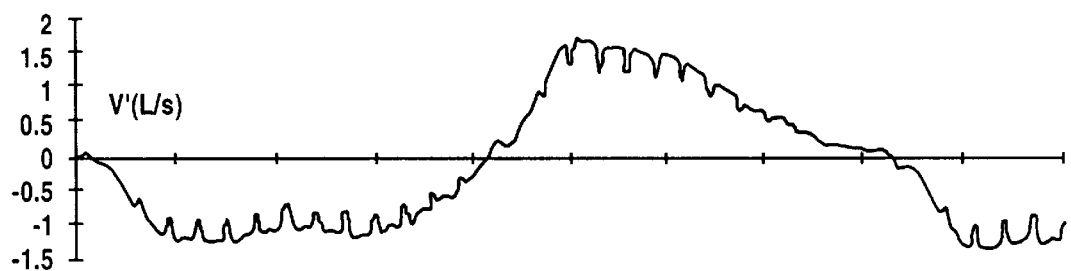
Figure 13C:
Figure 13D:
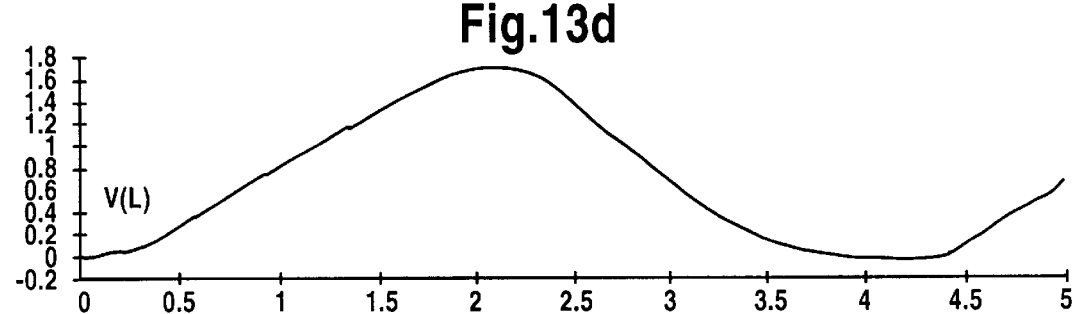

FIGS. 13a–13d disclose a typical five second acquisition; FIG. 13a is mouth pressure, FIG. 13b is flowrate, FIG. 13c is device resistance, and FIG. 13d is lung volume relative to functional residual volume.

Five functions handle processing of the raw data buffers. They are called ApplyCalibration, CalculateLungVolume, FindPerturbations, GetVirtualData, and CalcResistance.

ApplyCalibration splits the buffer into 32-bit single-precision floating-point decimal arrays of pressure data and flow data. The calibration factors are applied to obtain units of $cmH_2O$ and L/s for the arrays. Two new arrays are also created. One is device resistance ($R_{dev}$), the mouth pressure divided by flowrate. Device resistance is pneumotach resistance when flow is unperturbed; it is pneumotach resistance plus screen resistance (if a screen is present) during perturbation. The other new array is the derivative of device resistance ($R'_{dev}$), calculated as the centered numerical derivative, or the slope of the chord between the previous data point and the subsequent data point. It is used to detect the beginning and end of perturbation.

CalculateLungVolume calculates an array of instantaneous lung volume estimates for each data point in the acquisition. The lung volumes are taken relative to end-expiratory volume. The function finds the first instance of flow reversal from exhalation to inhalation and assigns it a volume of zero. It then integrates flow forward and backward in time from that point. Inhaled volume is multiplied by a body temperature, standard pressure, saturated (BTPS) volume correction factor.

Figure 14A:
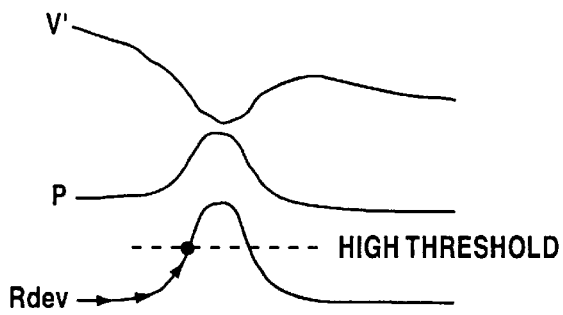
FIGS. 14a–14f illustrate operations of various functions of the present invention.

FindPerturbations detects the starting and ending points of the perturbation. It takes advantage of the fact that mouth pressure divided by flowrate is equal to the resistance of the perturbation mechanism ($R_m$). This resistance is usually pneumotach resistance, about 0.40 $cmH_2O/L/s$. During a perturbation, it is pneumotach resistance plus any screen resistance. The function detects the occurrence of a perturbation by looking for instances where $R_{dev}$ exceeds a threshold resistance of 0.65 $cmH_2O/L/s$ (FIG. 14a). The function then looks backward (FIG. 14b) and forward (FIG. 14c) in time to find the closest instances on a non-perturbed state. A non-perturbed state is indicated by an $R_{dev}$ less than the threshold and an $R'_{dev}$ near zero. The starting and ending time of each perturbation is saved to the sheet "Out." Regions of data where flowrate is less than 0.25 L/s are ignored by this function. The signal-to-noise ratio of the perturbations are too low to be useful.

Figure 14D:
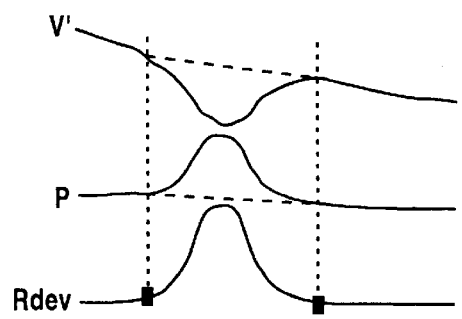
Figure 14B:
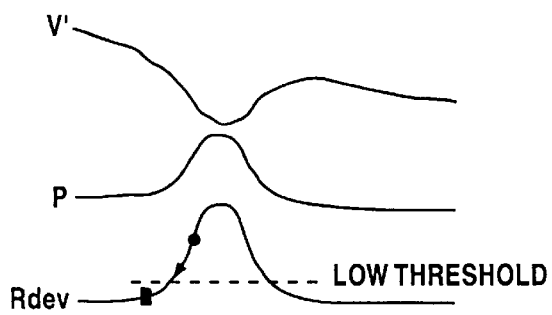

GetVirtualData derives an equation for virtual data, or an estimate of what mouth pressure and flowrate would have been had no perturbation occurred. These are linear curves between the data points immediately preceding and immediately following the perturbation (FIG. 14d).

Figure 14E:
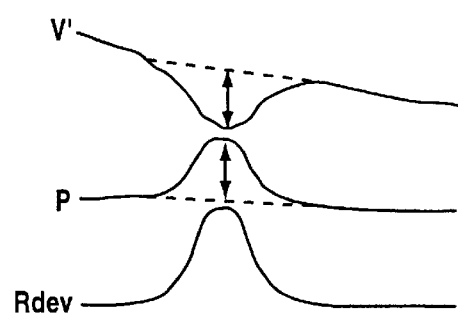
Figure 14C:
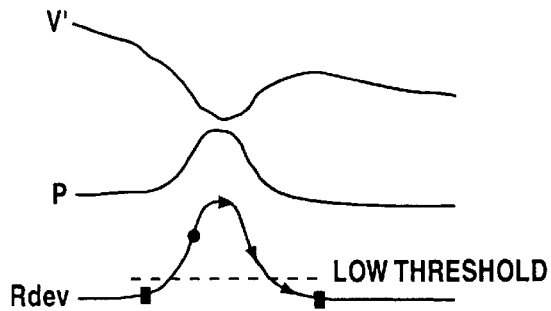

CalcResistance uses the real and virtual data to find respiratory resistance. This function finds the instant of minimum flowrate magnitude and calculates pressure perturbation magnitude ($\Delta P$) and flow perturbation magnitude ($\Delta V'$). At this point air volume acceleration is closest to zero, minimizing the mass inertia contribution to pressure drop. The ratio of these numbers is respiratory resistance (FIG. 14e). If the $\Delta V'$ is less than 0.25 L/s, or the $\Delta P_m$ is less than 0.1 $cmH_2O$, then resistance is ignored. Otherwise, the function saves virtual flowrate, real flowrate, virtual mouth pressure, real mouth pressure, lung volume, and respiratory resistance to the sheet "Out."

Figure 14F:
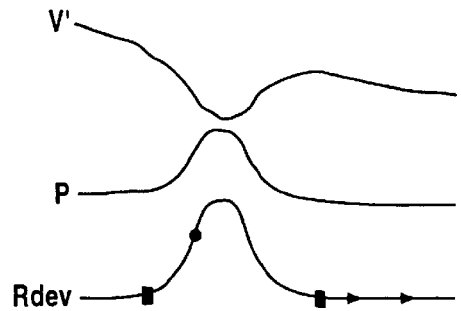

FindPerturbations inspects the five-second acquisition sequentially from first data point to last data point. It calls GetVirtualData and CalcResistance as each perturbation is detected (FIG. 14f). In other words, FIGS. 14a–14f illustrate operations of APDRT functions FindPerturbations GetVirtualData, and CalcResistance.

There is a series of mechanical model configurations that were utilized in order to perform a series of tests to determine APD accuracy and reliability. The APD operates under the assumption that resistance is constant during the perturbation. In other words, pressure drop across the system is linearly related to flowrate. The presence of a positive $K_2$ would lead to over estimates of $R_{APD}$ compared to actual resistance. An estimate of pressure drop across the model ($P_{APD}$) was calculated for each $R_{APD}$ by multiplying the $R_{APD}$ by the virtual flowrate at the time of perturbation. The values for a series of configurations which were tested were consistently higher than actual pressure. This indicates that model airflow resistance is flowrate dependent during the perturbation.

Figure 15:
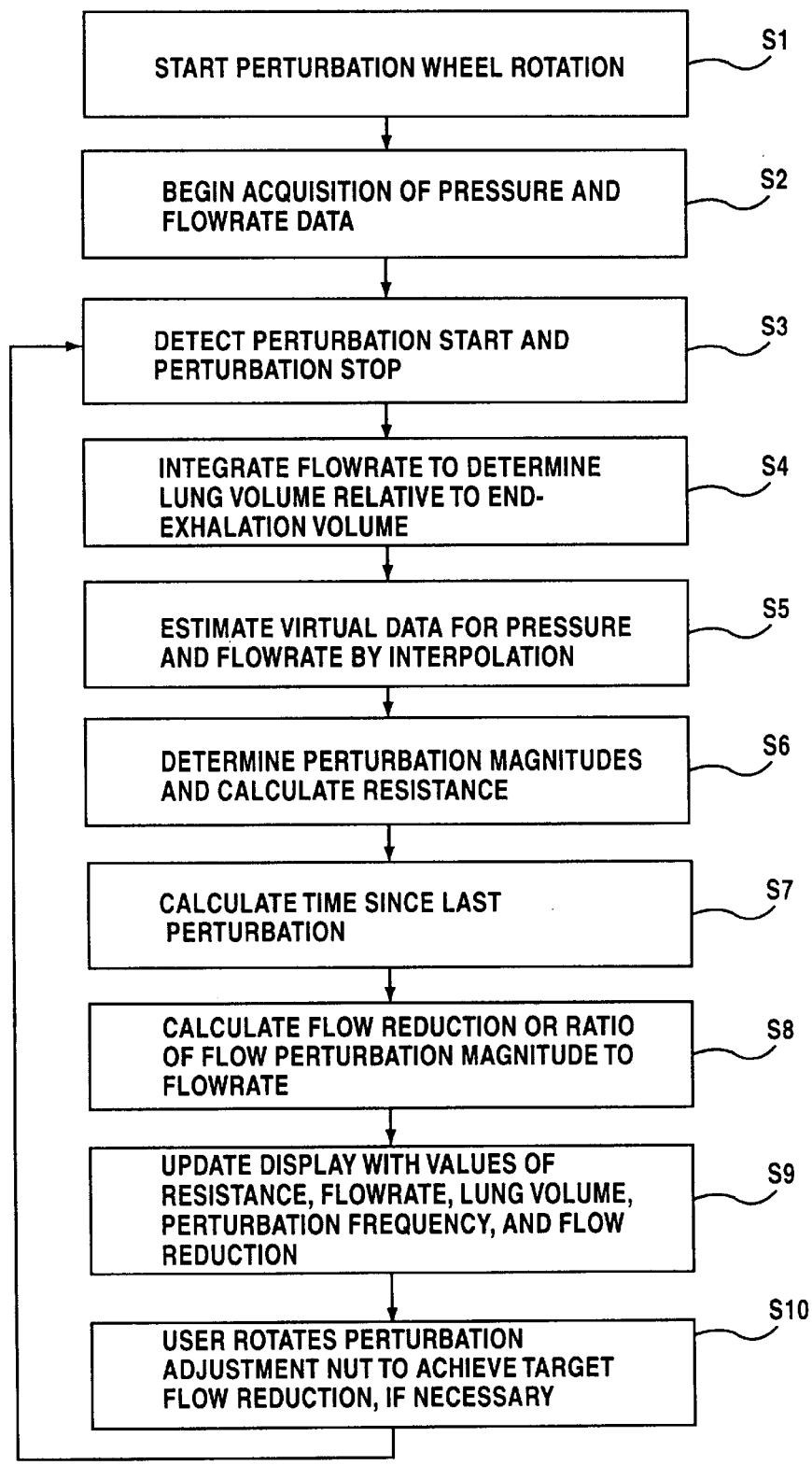
FIG. 15 illustrates a process of determining respiratory parameters according to the invention.

FIG. 15 is a flowchart explaining the procedure for obtaining respiratory resistance data, and therefore calculating other respiratory parameters of a patient, using a device, system, and method according to the present invention. At step S1, perturbation wheel rotation is started through the application of voltage to motor 6. A subject or patient then breathes normally (while holding cheeks) into the mouthpiece or pneumotach, thereby causing the pressure taps to provide differential pressure data to transducers 2 and 4, which provide signals to the data acquisition computer at step S2. At step S3, the data acquisition computer detects perturbation start and perturbation stop, as discussed previously. Using mathematical integration of flowrate, lung volume is determined relative to end-exhalation volume, and virtual data is estimated for pressure and flowrate by interpolation (step S5). At step S6, perturbation magnitudes are determined, and respiratory resistance is calculated. At step S7, the data acquisition computer calculates the time since the last perturbation, and at step S8 flow reduction or ratio of flow perturbation magnitude to flowrate is calculated. At step S9, the display of the data acquisition computer is updated with calculated values of resistance, flowrate, lung volume, perturbation frequency, and flow reduction. The user or the technician can, at this point, or at any point, during the data acquisition and test, can rotate the perturbation adjustment nut if the embodiment of FIGS. 5–7 is used in order to achieve a target flow reduction, and to otherwise match device resistance to respiratory resistance of the patient. The effect of rotating the nut can be seen as a change in flow reduction on the display of the computer. Testing can then be repeated as necessary, to generate appropriate respiratory resistance data, flowrate data, lung volume data, etc., as may be necessary for the particular subject (step S10).

During human subject testing, the APD was mounted on an appropriate stand, and each subject inhaled and exhaled through the APD via a mouthpiece. Nose clips were used, and the subject firmly supported their cheeks with their hands. The subject was instructed to keep their glottis open and their tongue still, in its normal resting position. The subject was instructed to breath normally, and the APD was operated with a wheel speed equivalent to 6.7 perturbations per second. The subject breathed through the APD until 100 inspiratory and 100 expiratory perturbations were obtained, which took approximately one minute. The data acquisition computer, through the APDRT software, calculated $R_{APD}$ for each perturbation, as discussed above, an average inspiratory resistance and average expiratory resistance $R_{ABG,\ IN}$ and $R_{ABG,\ EX}$ were then calculated. If the standard deviation of the $R_{APD}$ values were noted to be high, the test was repeated. Such high standard deviation could occur if excessive electrical noise was present in the power supply, or if any breathing anomalies were introduced during the measurement, such as a hiccup, cough, or closing of the glottis.

Significant additional testing of the APD has shown that the APD measures resistance consistently and accurately in humans as well as in mechanical models. The values which are provided by the APD, system and method of the present invention are similar to those values which are obtained by such techniques as the forced oscillation techniques of the prior art, but the results are more easily and more quickly obtainable with the present invention. An APD according to the invention, therefore, can be used in such varied settings as a bedside device in an intensive care unit, at an accident scene for monitoring the respiratory condition of trauma victims, for routine screening tests in physician's offices and outpatient clinics, as well as occupational health clinics for monitoring exposure to airborne contamination, and other various applications.

The present invention, as discussed above, provides numerous advantages over other respiratory diagnostic devices. The embodiments of the invention are small, lightweight, and inexpensive, and utilize perturbation data to generate respiratory resistance, as a function of parameters which were not known in the art to generate respiratory resistance data. Respiratory resistance was not previously determinable as a function of lung volume or flowrate in reasonable clinical applications. Additionally, the separate determination and storage of inhalation and exhalation resistance is an advantage which is provided by the configuration of the present invention. Additionally, due to the light weight and simplicity of the invention, it is possible to continuously monitor respiratory resistance through continued normal breathing into an airflow perturbation device according to the invention. Continuous monitoring would enable a better determination, for example, of the effect of bronchodilator drugs. Prior art resistance devices such as body plethysmography did not enable any such continuous monitoring.

The above-discussed embodiments of the invention are for illustrative purposes only, and are not intended to limit the invention. Various equivalents and substitutions can be made, and still remain within the spirit and scope of the invention. For example, the determination of respiratory resistance as discussed above is one way of doing so. It would be within the purview of the person of ordinary skill in the art to utilize spectral analysis, or another mathematical analysis, in order to determine respiratory resistance. Additionally, respiratory resistance can be calculated as a function of frequency or of perturbation rate, with perturbation rate varying based upon the speed of rotation of the segmented wheel, or otherwise varying the perturbation rate. The analysis of frequency characteristics can be shown to effect resistance. Sweeping of perturbation frequency can be used to provide frequency/resistance data. The metes and bounds of the invention, therefore, are to be determined based upon the appended claims.

We claim:

1. An airflow perturbation device, comprising:
    a housing;
    an airflow/differential pressure conversion device on an input side of said housing, said airflow/differential pressure conversion device having an input and an output and first and second pressure taps thereupon;
    an alternating perturbation mechanism movably attached to said housing and disposed at the output of said airflow/differential pressure conversion device, said alternating perturbation mechanism alternatingly blocking and unblocking the output of the airflow/differential pressure conversion device;
    a moving device attached to said housing for moving said alternating perturbation mechanism;
    a first pressure transducer connected to said first differential pressure tap for determining a first differential pressure;
    a second pressure transducer attached to said second differential pressure tap for determining a second differential pressure; and
    a perturbation adjustment mechanism on the input side of the housing, said perturbation adjustment mechanism for adjusting a perturbation level, said perturbation level determined based upon output from the first and second pressure transducers,
    said first and second pressure transducers providing an output signal which is provided to a signal processing means for determining parameters associated with a respiratory system of a patient inhaling and exhaling through the airflow/differential pressure conversion device.

2. An airflow perturbation device as recited in claim 1, wherein said airflow/differential pressure conversion device comprises a pneumotach.

3. An airflow perturbation device as recited in claim 1, wherein said perturbation adjustment mechanism comprises an input tube on the input side of the housing, said airflow/differential pressure conversion device being inserted into the input tube, said input tube having a threaded outer peripheral surface, with at least one aperture through a wall of the tube, and a rotatable adjustment nut engaging said threaded outer peripheral surface, wherein rotation of said nut results in selective constriction of said at least one aperture.

4. An airflow perturbation device as recited in claim 1, wherein said alternating perturbation mechanism comprises a segmented wheel disposed in said housing, said segmented wheel including at least one open segment which, when aligned with the output of the airflow/differential pressure conversion device, enables unrestricted airflow therethrough, and at least one blocking segment which, during rotation of the segmented wheel, at least partially blocks the output of the input side of the device, and wherein said moving device comprises a motor driveably connected to the segmented wheel, wherein a rotation of the motor results in a rotation of the segmented wheel such that the at least one open segment and the at least one blocking segment are alternatingly aligned with said output of the input side of the device.

5. An airflow perturbation device as recited in claim 4, wherein said moving means comprises a motor having a gear reduction thereupon, and wherein said segmented wheel is attached to an output shaft of said gear reduction.

6. An airflow perturbation device as recited in claim 4, wherein said segmented wheel is rotationally attached to said housing, and wherein said segmented wheel is attached to an output of said motor by a drive belt, wherein a relationship of a size of the segmented wheel to a size of an output pulley attached to the motor results in a gear reduction.

7. An airflow perturbation device as recited in claim 1, wherein said alternating perturbation mechanism comprises a segmented wheel disposed in said housing, said segmented wheel including at least one screened segment which, when aligned with the output of the airflow/differential pressure conversion device, enables perturbed airflow therethrough, and at least one open segment, which, during rotation of the segmented wheel, enables substantially unrestricted airflow therethrough, and wherein the moving device comprises a motor driveably connected to the segmented wheel, wherein a rotation of the motor results in a rotation of the segmented wheel such that the at least one screened segment and the at least one open segment are alternatingly aligned with the output of the input side of the device.

8. An airflow perturbation device as recited in claim 1, wherein said housing comprises metal.

9. An airflow perturbation device as recited in claim 1, wherein said housing comprises nylon.

10. An airflow perturbation device as recited in claim 1, wherein said housing comprises plastic.

11. An airflow perturbation system, comprising:
an airflow perturbation device for generating signals regarding respiratory parameters of a patient, said airflow perturbation device including an input device for receiving exhaled air from the patient, said input device comprising an airflow/differential pressure conversion device on an input side of a housing of the airflow perturbation device, with the airflow/differential pressure conversion device having first and second pressure taps thereupon;
a data acquisition device connected to said airflow perturbation device, said data acquisition device acquiring the signals output from the airflow perturbation device, said data acquisition device including storage means for storing a plurality of sets of data over a predetermined period of time, said data acquisition device including a processing device for calculating at least one of lung volume of the patient, perturbation data, virtual data, and respiratory resistance;
an alternating perturbation mechanism movably attached to said housing and disposed at an output of said airflow/differential pressure device, said alternating perturbation mechanism alternatingly blocking and unblocking the output of the airflow/differential pressure device;
a moving device attached to the housing for moving said alternating perturbation mechanism;
a first pressure transducer connected to said first differential pressure tap for determining a first differential pressure;
a second pressure transducer attached to said second differential pressure tap for determining a second differential pressure, said first and second pressure transducer each providing an output signal provided to said data acquisition device, wherein said data acquisition device stores the plurality of sets of data from the first and second pressure taps over the predetermined period of time, and said processing device calculating the at least one of lung volume, perturbation data, virtual data, and respiratory resistance based upon the output from the first and second pressure transducers and
a perturbation adjustment mechanism on the input side of the housing, said perturbation adjustment mechanism for adjusting a perturbation level of the airflow perturbation device, said perturbation level being adjusted so that a device resistance provided by said airflow perturbation device provides an appropriate sensitivity based upon a respiratory resistance of a patient.

12. An airflow perturbation system as recited in claim 11, wherein said processing device includes a calibration means for providing a calibration.

13. An airflow perturbation system as recited in claim 11, wherein said processing device includes means for calculating respiratory resistance according to the formula:

$$R = \frac{\Delta P}{\Delta V'}$$

wherein R equals resistance in cmH$_2$O/L/s, $\Delta P$ is mouth pressure perturbation magnitude, and $\Delta V'$ is flow perturbation magnitude.

14. An airflow perturbation system as recited in claim 11, wherein said processing device comprises respiratory resistance calculating means for calculating respiratory resistance as a function of lung volume, based upon data provided by output from said first and second pressure transducers.

15. An airflow perturbation system as recited in claim 11, wherein said data acquisition device includes first storage means for storing exhalation data provided by said first and second pressure transducers, and inhalation data storage means for storing inhalation data provided by said first and second pressure transducers, said data acquisition device further comprising exhalation resistance calculating means for calculating an exhalation resistance based upon said exhalation data stored in said first storage means.

16. An airflow perturbation system as recited in claim 15, wherein said data acquisition device includes inhalation resistance calculating means for calculating an inhalation resistance of the patient based upon the output from the first and second pressure transducers.

17. An airflow perturbation system as recited in claim 11, wherein said processing device comprises respiratory resistance calculating means for calculating respiratory resistance as a function of volumetric flowrate based upon output of the first and second pressure transducers.

18. An airflow perturbation system as recited in claim 11, further comprising continuous monitoring means for continuously monitoring input from said first and second pressure transducers.

19. An airflow perturbation system as recited in claim 11, wherein said first pressure transducer is connected to said first differential pressure tap and said second differential pressure tap, for determining said first differential pressure as a differential pressure between the outputs of the first and second differential pressure taps, and wherein said second differential pressure transducer is connected to said second differential pressure tap for determining said second differential pressure as mouth pressure relative to atmosphere pressure.

20. A method for determining respiratory parameters of a patient, said method comprising the steps of:
generating airflow perturbation signals from an airflow perturbation device based upon inhalation and exhalation of a patient;
adjusting a perturbation level of the airflow perturbation device such that a device resistance provides an appropriate sensitivity based upon a respiratory resistance of a patient;
inputting said signals into a data acquisition computer;
determining a start and stop of a perturbation generated in said airflow determination device;
estimating virtual data for pressure and flowrate of non-perturbed airflow;
determine perturbation magnitude based upon the perturbation data and the estimated virtual data;
calculating respiratory resistance based upon said perturbation magnitudes and said virtual data;
storing said calculation resistance in a memory, as a stored resistance value.

21. A method as recited in claim 20, further comprising a step of calculating respiratory resistance as a function of flowrate.

22. A method as recited in claim 20, further comprising a step of calculating respiratory resistance as a function of lung volume.

23. A method as recited in claim 20, further comprising the steps of:
separately storing inhalation perturbation data and exhalation perturbation data;
calculating an exhalation resistance based upon the stored exhalation perturbation data; and calculating inhalation resistance based upon the stored inhalation perturbation data.

24. A method as recited in claim 20, comprising a further step of calculating a volumetric flowrate based upon the respiratory resistance.

25. A method as recited in claim 20, comprising a further step of continuously repeating the calculation of respiratory resistance in order to continuously monitor respiratory parameters of the patient.

26. A computer program for determining respiratory parameters of a patient, said computer program embodied on a computer readable medium, and controlling a data acquisition computer and a respiratory resistance measuring device to perform the steps of:

generating airflow perturbation signals from an airflow perturbation device based upon inhalation and exhalation of a patient;

adjusting a perturbation level of the airflow perturbation device such that a device resistance provides an appropriate sensitivity based upon a respiratory resistance of a patient;

inputting said signals into a data acquisition computer;

determining a start and stop of a perturbation generated in said airflow determination device;

estimating virtual data for pressure and flowrate of non-perturbed airflow;

determine perturbation magnitude based upon the perturbation data and the estimated virtual data;

calculating respiratory resistance based upon said perturbation magnitudes and said virtual data;

storing said calculation resistance in a memory, as a stored resistance value.

* * * * *